United States Patent
Conway et al.

(10) Patent No.: US 9,816,074 B2
(45) Date of Patent: Nov. 14, 2017

(54) METHODS AND COMPOSITIONS FOR MODULATING NUCLEASE-MEDIATED GENOME ENGINEERING IN HEMATOPOIETIC STEM CELLS

(71) Applicant: Sangamo BioSciences, Inc., Richmond, CA (US)

(72) Inventors: Anthony Conway, Richmond, CA (US); Gregory J. Cost, Richmond, CA (US); Philip D. Gregory, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 47 days.

(21) Appl. No.: 14/807,183

(22) Filed: Jul. 23, 2015

(65) Prior Publication Data

US 2016/0024474 A1    Jan. 28, 2016

Related U.S. Application Data

(60) Provisional application No. 62/029,002, filed on Jul. 25, 2014, provisional application No. 62/036,454, filed on Aug. 12, 2014, provisional application No. 62/158,257, filed on May 7, 2015.

(51) Int. Cl.
| | |
|---|---|
| *C12N 15/00* | (2006.01) |
| *C12N 9/22* | (2006.01) |
| *A61K 35/28* | (2015.01) |
| *C12N 5/0789* | (2010.01) |

(52) U.S. Cl.
CPC ............ *C12N 5/0647* (2013.01); *A61K 35/28* (2013.01); *C12N 9/22* (2013.01); *C12N 2500/38* (2013.01); *C12N 2501/065* (2013.01); *C12N 2501/2306* (2013.01); *C12N 2501/999* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,789,538 | A | 8/1998 | Rebar et al. |
| 5,925,523 | A | 7/1999 | Dove et al. |
| 6,007,988 | A | 12/1999 | Choo |
| 6,013,453 | A | 1/2000 | Choo |
| 6,140,081 | A | 10/2000 | Barbas |
| 6,140,466 | A | 10/2000 | Barbas, III et al. |
| 6,200,759 | B1 | 3/2001 | Dove et al. |
| 6,242,568 | B1 | 6/2001 | Barbas, III et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,689,558 | B2 | 2/2004 | Case |
| 6,794,136 | B1 | 9/2004 | Eisenberg et al. |
| 6,824,978 | B1 | 11/2004 | Cox, III et al. |
| 6,903,185 | B2 | 6/2005 | Kim et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,030,215 | B2 | 4/2006 | Liu et al. |
| 7,067,317 | B2 | 6/2006 | Rebar et al. |
| 7,070,934 | B2 | 7/2006 | Cox et al. |
| 7,153,949 | B2 | 12/2006 | Kim et al. |
| 7,163,824 | B2 | 1/2007 | Cox, III et al. |
| 7,253,273 | B2 | 8/2007 | Collingwood et al. |
| 7,262,054 | B2 | 8/2007 | Jamieson et al. |
| 7,361,635 | B2 | 4/2008 | Miller et al. |
| 7,807,464 | B2 | 10/2010 | Zhang et al. |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 8,034,598 | B2 | 10/2011 | Miller et al. |
| 8,110,379 | B2 | 2/2012 | DeKelver et al. |
| 8,168,428 | B2 | 5/2012 | Zon et al. |
| 8,329,986 | B2 | 12/2012 | Butler et al. |
| 8,409,861 | B2 | 4/2013 | Guschin et al. |
| 8,563,314 | B2 | 10/2013 | Gregory et al. |
| 8,586,526 | B2 | 11/2013 | Gregory et al. |
| 8,623,618 | B2 | 1/2014 | Doyon et al. |
| 8,697,359 | B1 | 4/2014 | Zhang |

(Continued)

FOREIGN PATENT DOCUMENTS

| | | |
|---|---|---|
| EP | 1 669 441 A1 | 6/2006 |
| GB | 2338237 A | 12/1999 |

(Continued)

OTHER PUBLICATIONS van Rensburg et al., Chromatin structure of two genomic sites for targeted transgene integration in induced pluripotent stem cells and hematopoietic stem cells. Gene Therapy (2013) 20, 201-214.*

Ghule et al., Reprogramming the pluripotent cell cycle: restoration of anabbreviated G1 phase in human induced pluripotent stem (iPS) cells. Cell Physiol. May 2011; 226(5): 1149-1156.*

Huangfu et al., Induction of pluripotent stem cells by defined factors is greatly improved by small-molecule compounds. Nat Biotech, 2008, 26:795-797.*

Walasek et al., The combination of valproic acid and lithium delays hematopoietic stem/progenitor cell differentiation. Blood 2012 119:3050-3059.*

(Continued)

*Primary Examiner* — Christopher M Babic
*Assistant Examiner* — Arthur S Leonard
(74) *Attorney, Agent, or Firm* — Pasternak Patent Law; Susan Abrahamson

(57) ABSTRACT

The present disclosure is in the field of genome engineering, particularly targeted modification of the genome of a hematopoietic stem cell.

9 Claims, 19 Drawing Sheets

(56) References Cited

U.S. PATENT DOCUMENTS

| | | | |
|---|---|---|---|
| 8,735,153 | B2 | 5/2014 | Wolffe et al. |
| 8,741,640 | B2 | 6/2014 | Gao et al. |
| 8,772,009 | B2 | 7/2014 | Doyon |
| 8,956,828 | B2 | 2/2015 | Bonini et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2005/0267061 | A1 | 12/2005 | Martin |
| 2006/0063231 | A1 | 3/2006 | Li et al. |
| 2006/0188987 | A1 | 8/2006 | Guschin et al. |
| 2007/0218528 | A1 | 9/2007 | Miller |
| 2008/0131962 | A1 | 6/2008 | Miller |
| 2008/0159996 | A1 | 7/2008 | Ando et al. |
| 2008/0200862 | A1 | 8/2008 | Unger et al. |
| 2009/0054985 | A1 | 2/2009 | Anderson |
| 2009/0068164 | A1 | 3/2009 | Segal et al. |
| 2009/0305346 | A1 | 12/2009 | Miller |
| 2010/0047805 | A1 | 2/2010 | Wang |
| 2010/0218264 | A1 | 8/2010 | Cui et al. |
| 2011/0201055 | A1 | 8/2011 | Doyon et al. |
| 2011/0207221 | A1 | 8/2011 | Cost et al. |
| 2011/0263001 | A1* | 10/2011 | Lakshmipathy ....... C12N 15/86 435/235.1 |
| 2011/0265198 | A1 | 10/2011 | Gregory et al. |
| 2012/0017290 | A1 | 1/2012 | Cui et al. |
| 2013/0122591 | A1 | 5/2013 | Cost et al. |
| 2013/0136722 | A1 | 5/2013 | Mahmud |
| 2013/0137104 | A1 | 5/2013 | Cost et al. |
| 2013/0177960 | A1 | 7/2013 | Rebar |
| 2013/0177983 | A1 | 7/2013 | Rebar |
| 2014/0335063 | A1 | 11/2014 | Cannon et al. |
| 2015/0056705 | A1 | 2/2015 | Conway et al. |

FOREIGN PATENT DOCUMENTS

| | | | |
|---|---|---|---|
| WO | WO 95/19431 | A1 | 7/1995 |
| WO | WO 96/06166 | A1 | 2/1996 |
| WO | WO 98/37186 | A1 | 8/1998 |
| WO | WO 98/53057 | A1 | 11/1998 |
| WO | WO 98/53058 | A1 | 11/1998 |
| WO | WO 98/53059 | A1 | 11/1998 |
| WO | WO 98/53060 | A1 | 11/1998 |
| WO | WO 98/54311 | A1 | 12/1998 |
| WO | WO 00/27878 | A1 | 5/2000 |
| WO | WO 01/60970 | A2 | 8/2001 |
| WO | WO 01/88197 | A2 | 11/2001 |
| WO | WO 02/16536 | A1 | 2/2002 |
| WO | WO 02/077227 | A2 | 10/2002 |
| WO | WO 02/099084 | A2 | 12/2002 |
| WO | WO 03/016496 | A2 | 2/2003 |
| WO | WO 2007/014275 | A2 | 2/2007 |
| WO | WO 2010/025421 | A2 | 3/2010 |
| WO | WO 2010/079430 | A1 | 7/2010 |
| WO | WO 2012/149472 | A2 | 11/2012 |
| WO | WO 2014/015312 | A1 | 1/2014 |

OTHER PUBLICATIONS

Baudet, et al., RNAI Screen Identifies MAPK14 As a Druggable Suppressor of Human Hematopoietic Stem Cell Expansion, *Blood* 119(26):6255-6258 (2012).

Beerli, et al., "Engineering Polydactyl Zinc-Finger Transcription Factors," *Nature Biotechnol.* 20:135-141(2002).

Boch, et al., "Breaking the Code of DNA Binding Specificity of TAL-Type III Effectors," *Science* 326:1509-1512 (2009).

Boitano, et al., "Aryl Hydrocarbon Receptor Antagonists Promote the Expansion of Human Hematopoietic Stem Cells," *Science* 329(5997):1345-1348 (2010) doi: 10.1126/science.1191536.

Bonas, et al., "Genetic and Structural Characterization of the Avirulence Gene AVRBS3 From Xanthomonas Campestris PV. Vesicatoria," *Mol. Gen. Genet.* 218:127-136 (1989).

Breems, et al., "Stroma-Contact Prevents Loss of Hematopoietic Stem Cell Quality During Ex Vivo Expansion of CD341 Mobilized Peripheral Blood Stem Cells," *Blood* 91(1): 111-117 (1998).

Butler, et al., "Development of a Vascular Niche Platform for Expansion of Repopulating Human Cord Blood Stem and Progenitor Cells," *Blood* 120(6):1344-1347 (2012).

Certo, et al., "Coupling Endonucleases With DNA End-Processing Enzymes to Drive Gene Disruption" *Nature Methods* 9(10):973-975 (2012) doi: 10.1038/nmeth.2177.

Chaurasia, et al., "Epigenetic Reprogramming Induces the Expansion of Cord Blood Stem Cells," *Journal Of Clinical Investigation* 124(6):2378-2395 (2014).

Choo, et al., "Advances in Zinc Finger Engineering," *Curr. Opin. Struct. Biol.* 10:411-416 (2000).

Christian, et al., "TAL Effector Nucleases Create Targeted DNA Double-Strand Breaks," *Genetics* epub 10.1534/genetics.110.120717.

Cong, et al., "Multiplex Genome Engineering Using CRISPR/CAS Systems," Sciencexpress/10.1126/science.1231143 (2013).

de Lima, et al., "Transplantation of Ex Vivo Expanded Cord Blood Cells Using the Copper Chelator Tetraethylenepentamine: A Phase I/II Clinical Trial," *Bone Marrow Transplantation* 41(9):771-778 (2008).

Fares, et al., "UM171 Is A Novel and Potent Agonist of Human Hematopoietic Stem Cell Renewal," *Blood* 122(21):798 Abstract from Oral Session (2013).

Fares, et al., "Pyrimidoindole Derivatives Are Agonists of Human Hematopoietic Stem Cell Self-Renewal," *Science* 345(6203):1509-1512 (2014)

Guo, et al., "Directed Evolution of an Enhanced and Highly Efficient FOKI Cleavage Domain for Zinc Finger Nucleases" *Journal of Molecular Biology* 400(1):96-107 (2010).

Haft, et al., "A Guild of 45 CRISPR-Associated (CAS) Protein Families and Multiple CRISPR/CAS Subtypes Exist in Prokaryotic Genomes," *PLoS Comput Biol.* 1(6):474-483 (2005).

Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).

Horwitz, et al., "Umbilical Cord Blood Expansion With Nicotinamide Provides Long-Term Multilineage Engraftmen," *Journal of Clinical Investigations* 124(7):3121-3128 (2014).

Isalan, et al., "A Rapid, Generally Applicable Method to Engineer Zinc Fingers Illustrated by Targeting the HIV-1 Promoter," *Nat. Biotechnol.* 19:656-660 (2001).

Jansen, et al., "Identification of Genes That Are Associated With DNA Repeats in Prokaryotes," *Molecular Microbiology* 43(6):1565-1575 (2002).

Jinek, et al., "A Programmable Dual-RNA-Guided DNA Endonuclease in Adaptive Bacterial Immunity," *Science* 17(337):816-821 (2012).

Kay, et al., "A Bacterial Effector Acts As a Plant Transcription Factor and Induces a Cell Size Regulator," *Science* 318:648-651 (2007).

Keller, et al., "Hematopoietic Commitment During Embryonic Stem Cell Differentiation in Culture," *Mol. and Cellular Biology* 13(1):473-486 (1993).

Knapinska, et al., "Molecular Mechanisms Regulating MRNA Stability: Physiological and Pathological Significance" *Current Geonomics* 6(6):471-486 (2005).

Magin, et al., "Primary Cells as Feeder Cells for Coculture Expansion of Human Hematopoietic Stem Cells From Umbilical Cord Blood-A Comparative Study," *Stem Cells Development* 18(1):173-186 (2009).

Makarova, et al., "A DNA Repair System Specific for Thermophilic Archaea and Bacteria Predicted by Genomic Context Analysis," *Nucleic Acids Res.* 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).

(56) References Cited

OTHER PUBLICATIONS

Moscou, et al., "A Simple Cipher Governs DNA Recognition by TAL Effectors," *Science* 326:1501 (2009).
North, et al., "Prostaglandin E2 Regulates Vertebrate Haematopoietic Stem Cell Homeostasis," Nature 447(7147):1007-1011(2007) doi:10.1038/nature05883.
Olovnikov, et al., "Bacterial Argonaute Samples the Transcriptome to Identify Foreign DNA," *Mol. Cell*. 51(5):594-605 (2013)
Pabo, et al., "Design and Selection of Novel CYS2HIS2 Zinc Finger Proteins," *Ann. Rev. Biochem*. 70:313-340 (2001).
Pabst, et al., "Identification of Small Molecules That Support Human Leukemia Stem Cell Activity Ex Vivo," *Nat. Meth*. 11:436-442 (2014).
Schornack, et al., "Gene-For-Gene-Mediated Recognition of Nuclear-Targeted AVRBS3-Like Bacterial Effector Proteins," *J. Plant Physiol*. 163(3):256-272 (2006).
Segal, et al., "Custom DNA-Binding Proteins Come of Age: Polydactyl Zinc-Finger Proteins," *Curr. Opin. Biotechnol*. 12:632-637 (2001).
Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.
Signer, et al., "Haematopoietic Stem Cells Require a Highly Regulated Protein Synthesis Rate" *Nature* 509(7498):49-54 (2013)
Swarts, et al., "DNA-Guided DNA Interference by a Prokaryotic Argonaute" *Nature* 507(7491):258-261 (2014).
Tebas, et al., "Gene Editing of CCR5 in Autologous CD4 T Cells of Persons Infected With HIV" *New England Journal of Medicine* 370(10):901 (2014).
Vogel, et al., "A Bacterial Seek-And-Destroy System for Foreign DNA" *Science* 344:972-973 (2014).
Walasek, et al., "The Combination of Valproic Acid and Lithium Delays Hematopoietic Stem/Progenitor Cell Differentiation" *Blood* 119(13):3050-9 (2012).
Wang, et al., "Coupling Endonucleases With DNA End—Processing Enzymes to Drive Gene Disruption" 10(1):57-63 *Nature Reviews Genetics* (2009).
Wang, et al., "Rapamycin Relieves Lentiviral Vector Transduction Resistance in Human and Mouse Hematopoietic Stem Cells," Blood 124:913-923 (2014).
Watts, et al., "Hematopoietic Stem Cell Expansion Facilitates Multilineage Engraftment in a Nonhuman Primate Cord Blood Transplantation Model," *Exp. Hematol*. 40(3):187-196 (2012).
Yuan, et al., Crystal Structure of A. Aeolicus Argonaute, A Site-Specific DNA-Guided Endoribonuclease, Provides Insights Into RISC-Mediated MRNA Cleavage, *Molecular Cellular* 19:405-419 (2005).
Zhang, et al., "Angiopoietin-Like 5 and IGFBP2 Stimulate Ex Vivo Expansion of Human Cord Blood Hematopoietic Stem Cells As Assayed by NOD/SCID Transplantation," *Blood* 111(7):3415-3423 (2008).
Ghule, et al., "Reprogramming the pluripotent cell cycle: restoration of an abbreviated G1 phase in human induced pluripotent stem (iPS) cells," Journal of Cellular Physiology 226(5):1149-1156 (2011).
Huangfu, et al., "Induction of pluripotent stem cells by defined factors is greatly improved by small-molecule compounds," Nature Biotechnology 26(7):795-797 (2008).
van Rensburg, et al., "Chromatin structure of two genomic sites for targeted transgene integration in induced pluripotent stem cells and hematopoietic stem cells," Gene Therapy 20(2):201-214 (2013).
Walasek, et al., "The combination of valproic acid and lithium delays hematopoietic stem/progenitor cell differentiation," Blood 119:3050-3059 (2012).

* cited by examiner

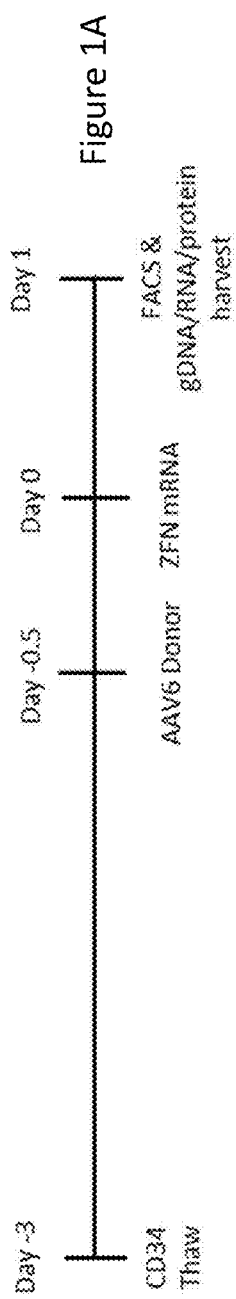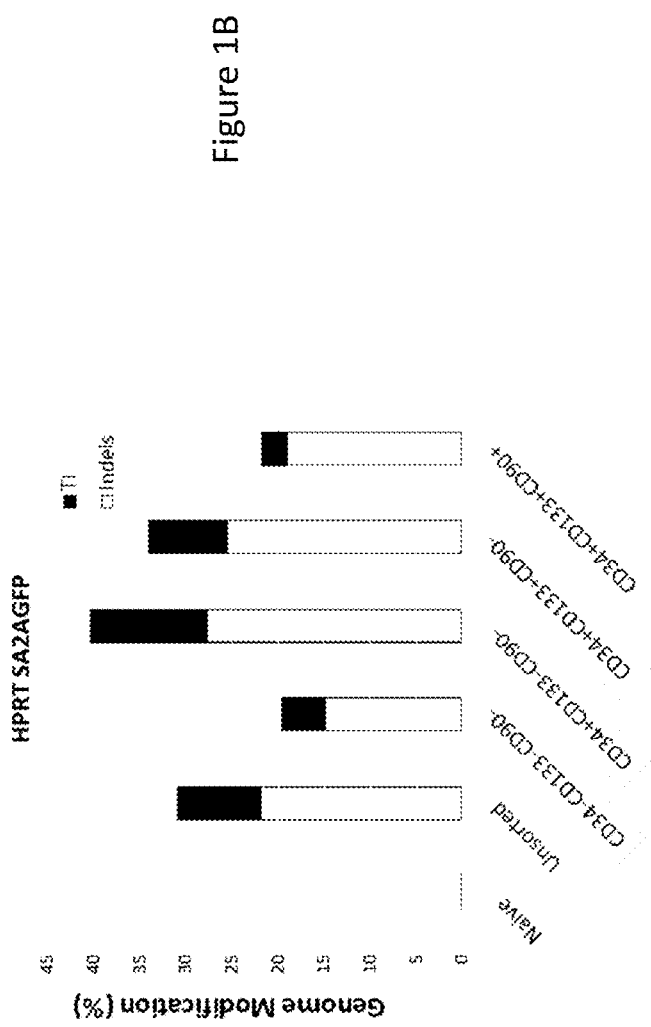

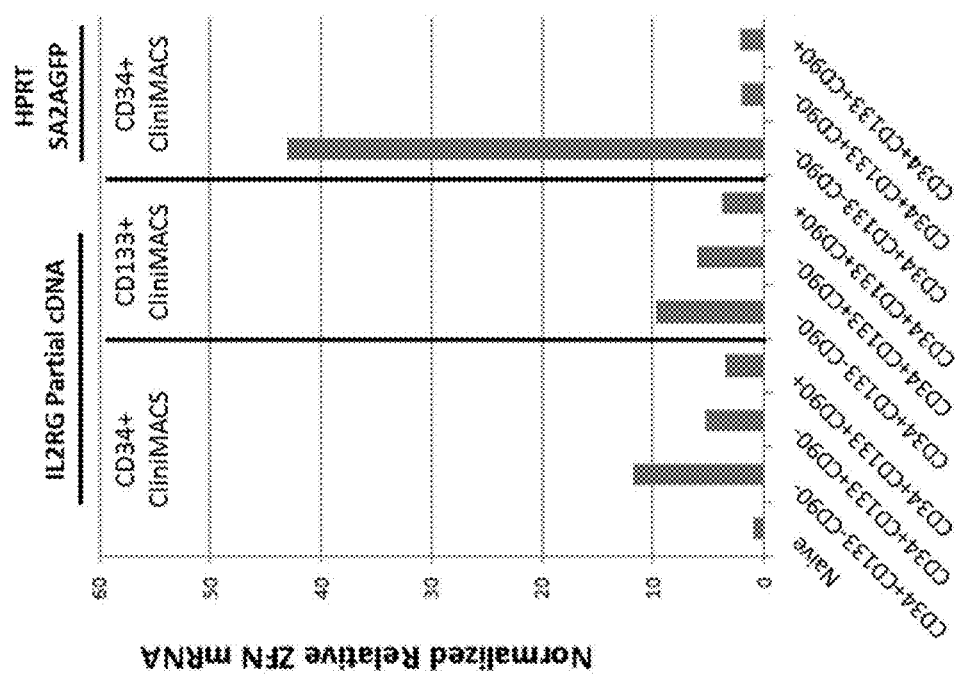

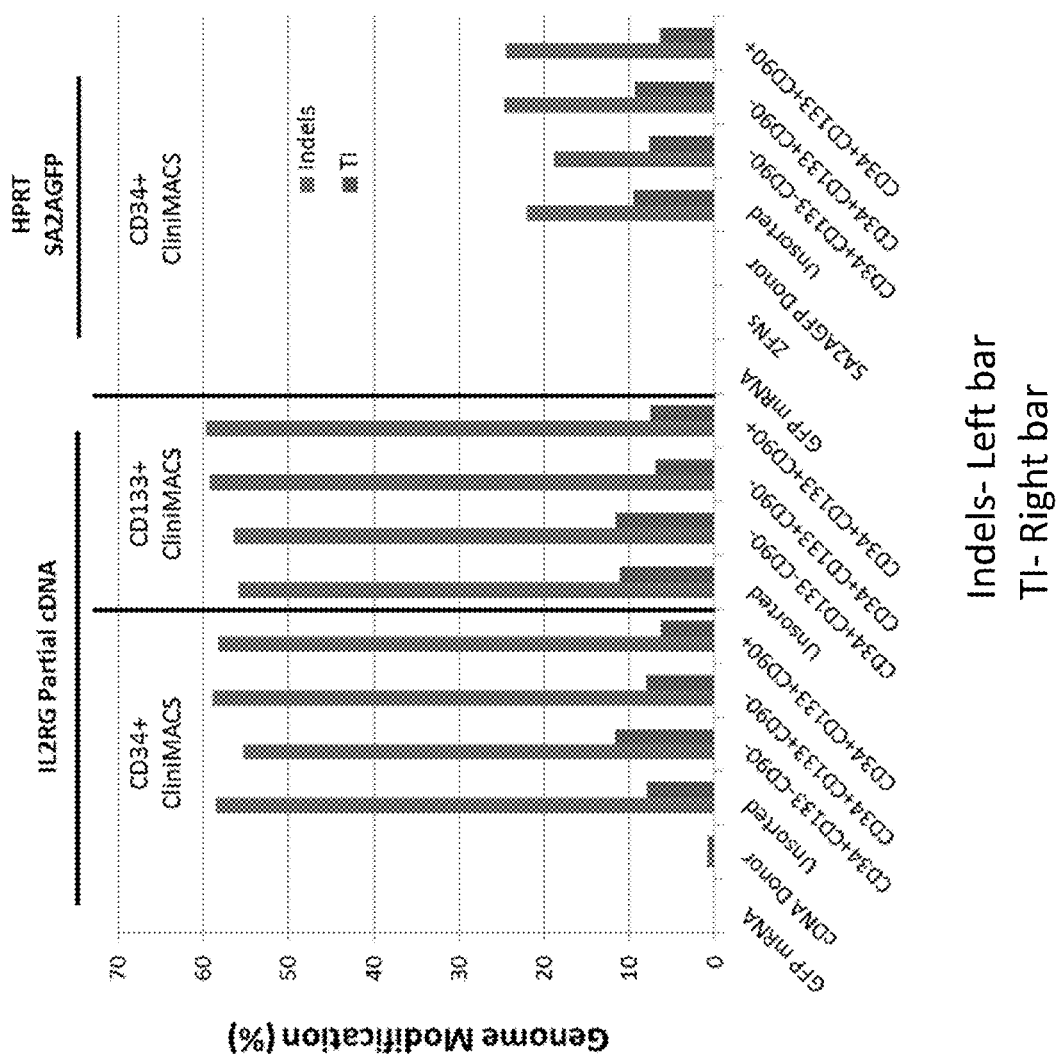

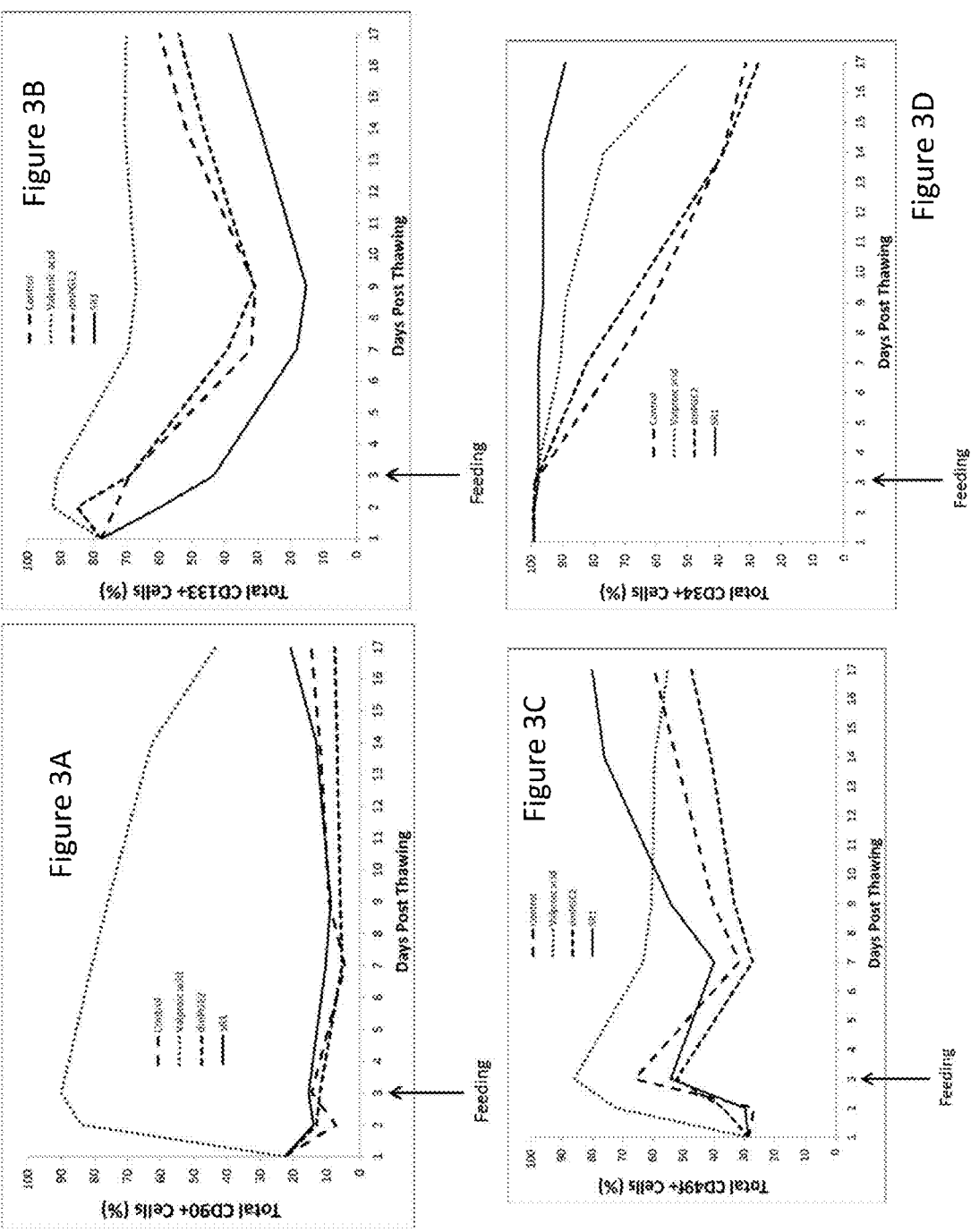

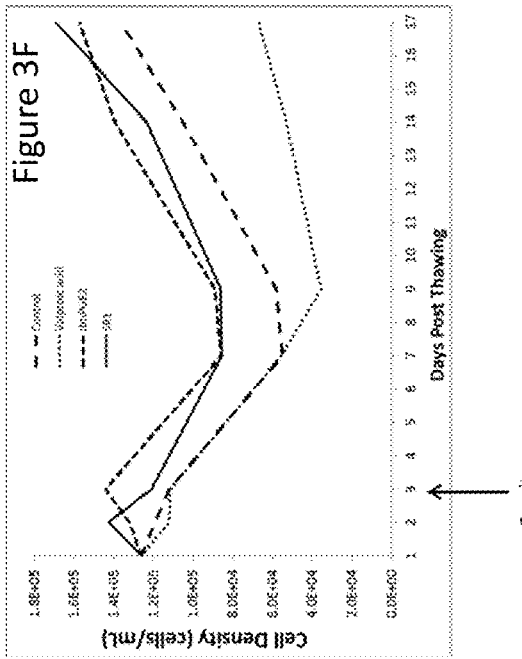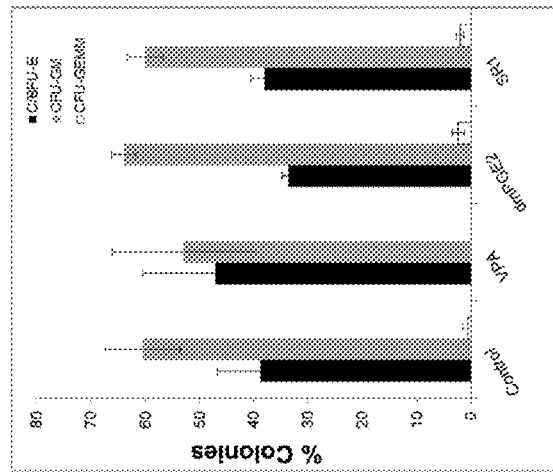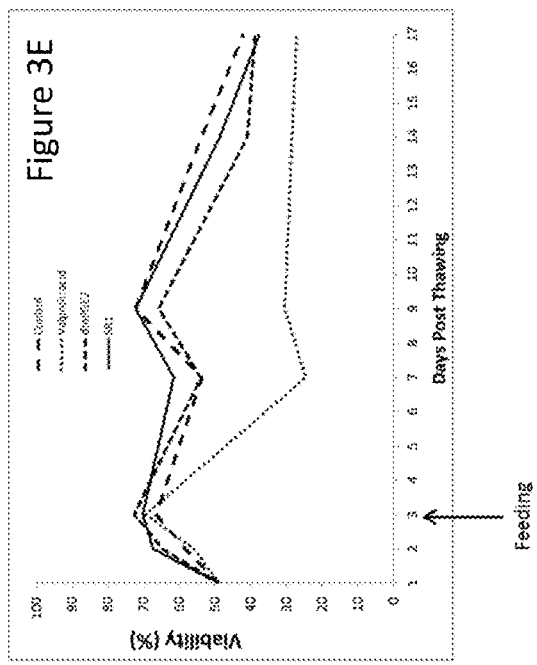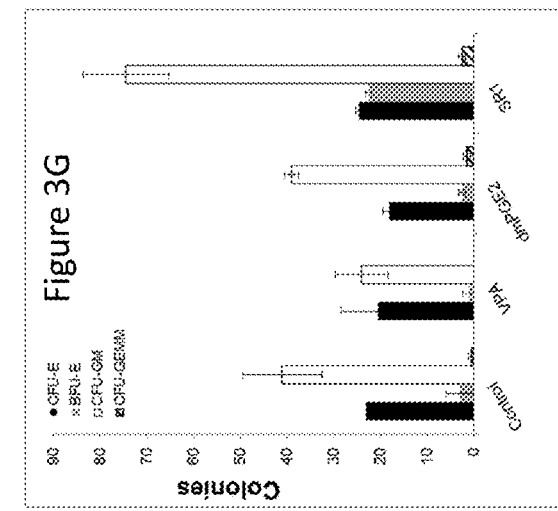

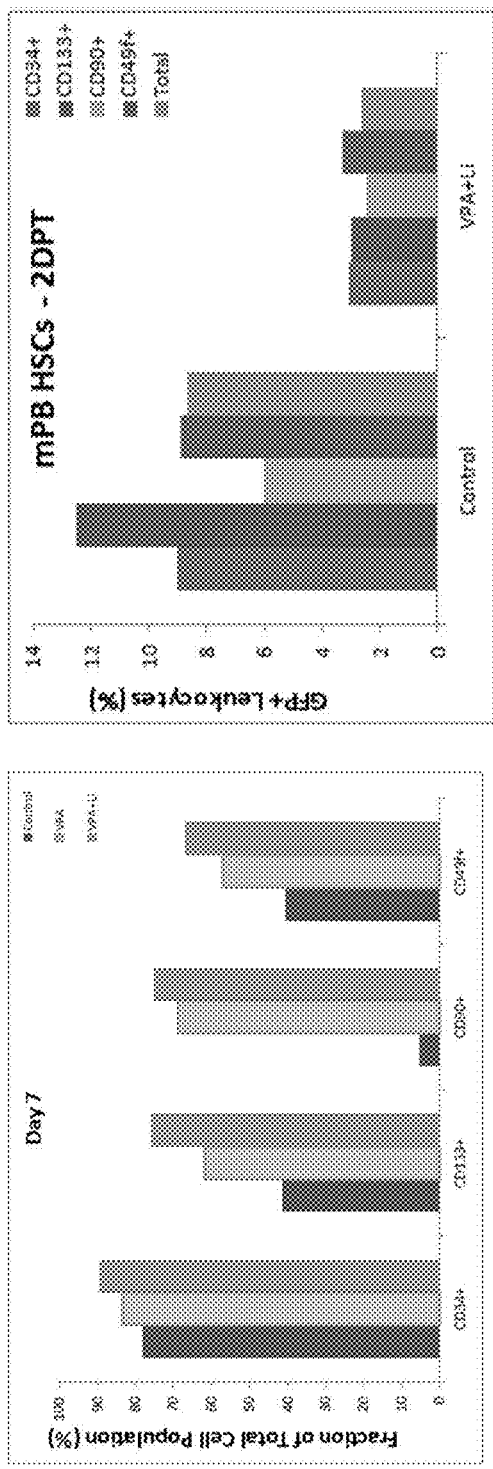
Figure 4B
Figure 4C
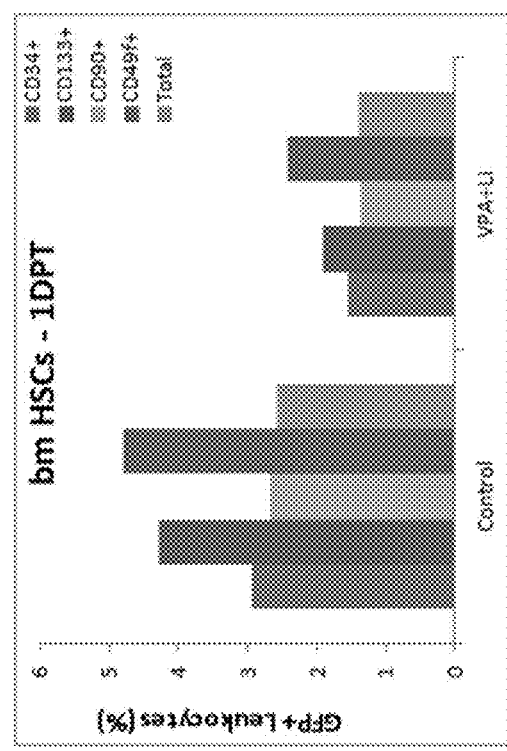
Figure 4D

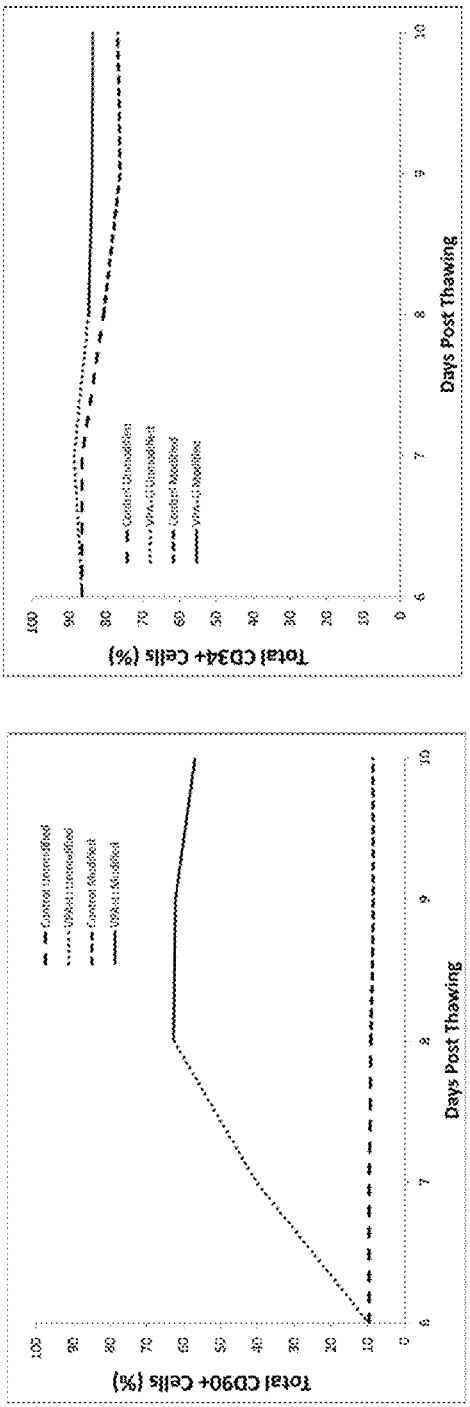
Figure 5A
Figure 5B
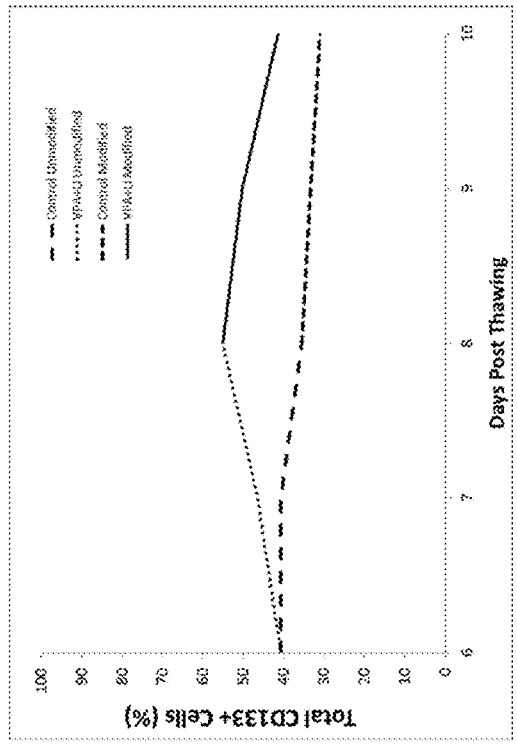
Figure 5C

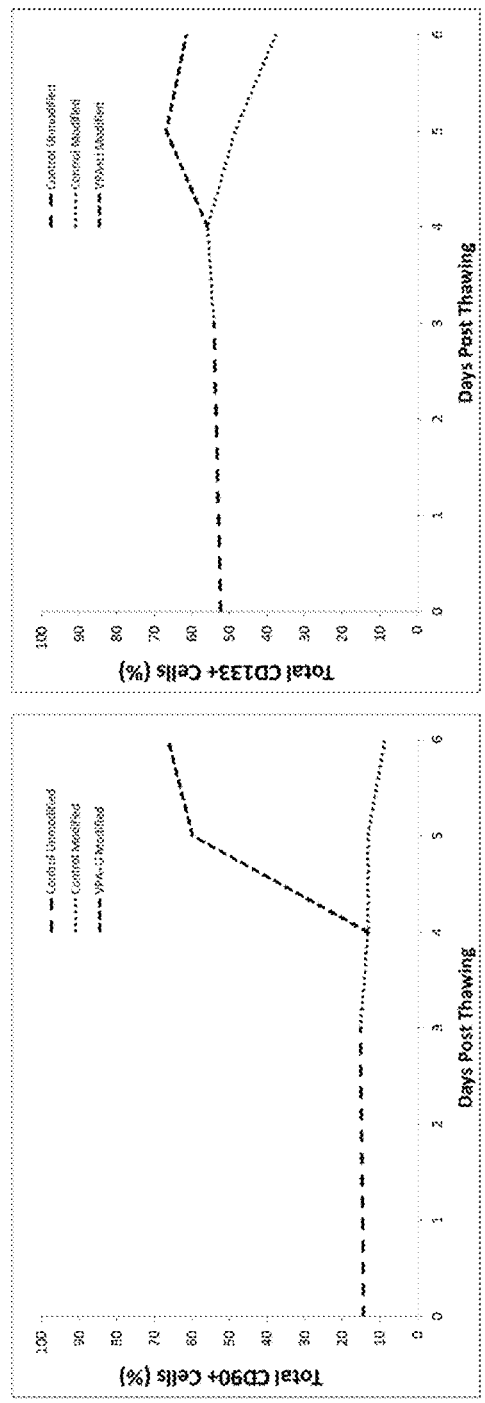
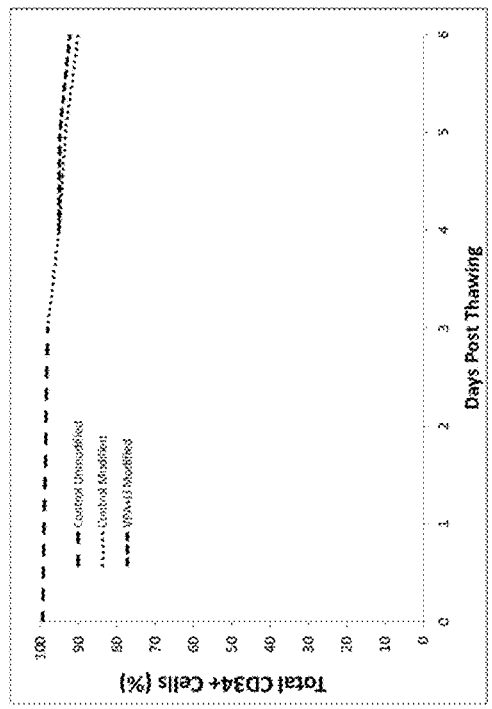
Figure 6A
Figure 6B
Figure 6C

METHODS AND COMPOSITIONS FOR MODULATING NUCLEASE-MEDIATED GENOME ENGINEERING IN HEMATOPOIETIC STEM CELLS

CROSS-REFERENCE TO RELATED APPLICATIONS

The present application claims the benefit of U.S. Provisional Application No. 62/029,002 filed Jul. 25, 2014; U.S. Provisional Application No. 62/036,454 filed Aug. 12, 2014; and U.S. Provisional Application No. 62/158,257 filed May 7, 2015, the disclosures of which are hereby incorporated by reference in their entireties.

TECHNICAL FIELD

The present disclosure is in the field of genome engineering, particularly targeted modification of the genome of a hematopoietic cell.

BACKGROUND

One of the most promising approaches in the gene therapy of a large number of diseases involves the use of in vitro genetic modification of stem cells followed by transplantation and engraftment of the modified cells in a patient. Particularly promising is when the introduced stem cells display long term persistence and multi-lineage differentiation. Hematopoietic stem cells, most commonly in the form of cells enriched based on the expression of the CD34 cell surface marker, are a particularly useful cell population since they can be easily obtained and contain the long term hematopoietic stem cells (LT-HSCs), which can reconstitute the entire hematopoietic lineage after transplantation.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus in cells from any organism. See, e.g., U.S. Pat. Nos. 8,956,828; 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983; 20130177960 and 20150056705, the disclosures of which are incorporated by reference in their entireties for all purposes. These methods often involve the use of engineered cleavage systems to induce a double strand break (DSB) or a nick in a target DNA sequence such that repair of the break by an error-prone process such as non-homologous end joining (NHEJ) or repair using a repair template (homology directed repair or HDR) can result in the knock out of a gene or the insertion of a sequence of interest (targeted integration). The repair pathway followed (NHEJ versus HDR or both) typically depends on the presence of a repair template and the activity of several competing repair pathways.

Introduction of a double strand break in the absence of an externally supplied repair template (e.g. donor) is commonly used for the inactivation of the targeted gene via mutations introduced by the cellular NHEJ pathway. NHEJ pathways can be separated into the standard Ku-dependent pathway and an alternative Ku-independent pathway based on micro-homology-mediated end joining, which takes advantage of short tracks of direct repeats near the cleavage site. The pattern of insertions and deletions ('indels') following gene editing via these two NHEJ pathways differ, which can result in differences in the functional consequences of the mutations, depending on the application.

In the presence of an externally supplied donor carrying stretches of homology to the sequences flanking the double strand break, homology directed gene repair (HDR), using the donor molecule, can be used to change the sequence of a single base or a small stretch of DNA (gene correction' or 'gene mutation') or, on the other extreme, for the targeted insertion of an entire expression cassette or fragment thereof (gene addition') into a pre-determined genomic location.

Cleavage can occur through the use of specific nucleases such as engineered zinc finger nucleases (ZFN), transcription-activator like effector nucleases (TALENs), or using the CRISPR/Cas system with an engineered crRNA/tracr RNA (single guide RNA') to guide specific cleavage. Further, targeted nucleases are being developed based on the Argonaute system (e.g., from *T. thermophilus*, known as 'TtAgo', see Swarts et at (2014) *Nature* 507(7491): 258-261), which also may have the potential for uses in genome editing and gene therapy.

Targeted cleavage using one of the above mentioned nuclease systems can be exploited to insert a nucleic acid into a specific target location using either HDR or NHEJ-mediated processes. However, delivering both the nuclease system and the donor to the cell can be problematic. For example, delivery of a donor or a nuclease via transduction of a plasmid into the cell can be toxic to the recipient cell, especially to a cell which is a primary cell and may not be as robust as a cell from a cell line.

CD34+ stem or progenitor cells are a biologically heterogeneous set of cells characterized by their ability to self-renew and/or differentiate into the cells of the lymphoid lineage (e.g. T cells, B cells, NK cells) and myeloid lineage (e.g. monocytes, erythrocytes, eosinophils, basophils, and neutrophils). Their heterogeneous nature arises from the fact that within the CD34+ stem cell population, there are multiple subgroups reflecting the multipotency (whether lineage-committed) of a specific group. For example, CD34+ cells that are also CD38− are more primitive, immature CD34+ progenitor cell, (also referred to as long-term hematopoietic progenitors), while those that are CD34+CD38+(short-term hematopoietic progenitors) are lineage-committed (see Stella et at (1995) *Hematologica* 80:367-387). When this population then progresses further down the differentiation pathway, the CD34 marker is lost. CD34+ stem cells have enormous potential in clinical cell therapy. However, in part due to their heterogeneous nature, performing genetic manipulations such as gene knock-out, transgene insertion, and the like upon the cells can be difficult. Specifically, these cells are poorly transduced by conventional delivery vectors, the most primitive stem cells are sensitive to modification, there is limited HDR following induced DNA DSBs, and there is insufficient HSC maintenance in prolonged standard culture conditions. Additionally, other cells of interest (for non-limiting example only, cardiomyocytes, medium spiny neurons, primary hepatocytes, embryonic stem cells, induced pluripotent stem cells and muscle cells) can be less successfully transduced for genome editing than others.

For both autologous and allogeneic HSC transplantation therapies, ex vivo culture of cells derived from human donors is often necessary. Depending on the cell source, the fraction of CD34+HSPCs can be quite low—approximately 0.0005%, 0.01%, or 0.1% for mobilized peripheral blood (mPB), bone marrow aspirate (BM), or cord blood, respectively. The fraction of long-term repopulating true stem cells (LT-HSCs) within these CD34+ cell populations is even lower (<1%). Furthermore, for autologous HSC therapies, autologous cord blood is often not available and thus mPB or BM-derived HSPCs are required. For an HSC transplant to have long-term efficacy the cells must engraft into the bone marrow and produce all of the hematopoietic lineages necessary for proper immune and red blood cell function. During in vitro culture, LT-HSCs often do not survive, do not proliferate, or differentiate into lineage-committed progenitors that will not result in long-term engraftment. Moreover, using currently-available techniques, it is often difficult to modify the genomes of LT-HSCs. Therefore, for HSC transplantation therapies to produce long-term efficacy, maintaining or increasing the overall amount of nuclease-modified LT-HSCs in culture is imperative.

Thus, there remains a need for compositions and methods for genome engineering of CD34+ cells, including LT-HCSs, and other stem or progenitor cells of interest that increase the efficiency of gene modification and provide cells comprising these genetic modifications.

SUMMARY

The present invention describes compositions and methods for use in gene therapy and genome engineering, particularly of hematopoietic cells, including HSCs. The present inventors have determined that certain culture conditions can impact the efficiency and the nature of gene modification after a double strand break (independent of the nuclease used), particularly in LT-HSCs.

In certain aspects, the methods and compositions described relate to influencing the genetic modification (e.g., repair outcome) following introduction of a double strand break in a target DNA of interest. Especially of interest is the use of these methods and compositions in hematopoietic stem cells/progenitor cells (HSC/PC). In addition, the methods and compositions of the invention are useful for the targeted integration of donor DNAs or the use of repair templates of interest in HSC/PC.

In some aspects, the invention provides for the use of a variety of compounds and methods that affect and/or increase stem cell expansion without loss of stemness and their maintenance that will also affect gene editing efficiency and DNA repair pathway choice in stem cells. In some embodiments, these methods and compositions are used to affect gene editing efficiency and DNA repair pathway choice in the LT-HSC subpopulation residing in CD34+ cell pools. In other embodiments, these methods and compositions are used to increase the overall percent of modified LT-HSC in a population of stem cells. Any factor(s) that affect(s) and/or increases stem cell expansion without loss of stemness can be used in the methods and compositions described herein. In some embodiments, small molecules and/or peptides are used to enhance stem cell expansion without loss of stemness, and thus enhance editing efficiency of a population or subpopulation of stem cells, as well as affecting the choice of repair pathway. In certain embodiments, the factors are selected from the group consisting of SR1, an aryl hydrocarbon receptor antagonist, dmPGE2, a prostaglandin, UM171 and UM729, compounds identified in a library screen (see Pabst et at (2014) *Nat Meth* 11:436-442), rapamycin (see Wang et at (2014) *Blood.* pii: blood-2013-12-546218), angiopoietin-like proteins ("Angptls", e.g. Notch/delta/ANGPTL5 (see Zhang et at (2008) *Blood.* 111(7):3415-3423), Angptl2, Angptl3, Angptl5, Angptl7, and Mfap4), the copper chelator tetraethyletepentamine (TEPA, see de Lima et at (2008) *Bone Mar Trans* 41:771-778), histone deacetylase (HPAC) inhibitors, e.g. valproic acid (see Chaurasia et at (2014) *J Clin Invest* 124:2378-2395), IGF-binding protein 2 (IGFBP2), nicotinamide (see Horwitz et at (2014) *J. Clin. Invest* 124:3121-3128), Tat-myc (see WO2010025421) and tat-Bcl2 (see WO2014015312) fusion proteins, MAPK14/p38a Ly2228820 (see Baudet et at (2012) *Blood* 119(26):6255-6258), products of self-renewing genes such as HOXB4, OCT3/4 cord blood and/or MSC derived feeder layers or an ex vivo vascular niche co-culture system termed E4+EC (see Butler et al (2012) *Blood.* 120(6): 1344-1347), cytokines, (by way of non-limiting example Stemspan™ CC110, CC100, and/or H3000 (Stemcell™ technologies), Flt-3 ligand, SCF, TPO). These methods and factors act of different cellular pathways to balance self-renewal and differentiation of stem cells, thus combinations may lead to potential synergistic activity. Similar and in some cases additive effects can be obtained when several of these factors are used in combination. In certain embodiments, the factors are added to the culture media and/or introduced directly into the cell. In some embodiments, the factors may be expressed from an endogenous gene, for example by introducing non-naturally occurring transcription factors (and/or nucleic acids encoding such transcription factors) to modulate expression of an endogenous gene involved in stem cell proliferation. See, e.g., U.S. Pat. No. 8,735,153 regarding modulation of endogenous genes involved in stem cell proliferation. In other embodiments, the factors are encoded by one or more nucleic acids that are introduced into the cell, for example from a donor molecule that is integrated via nuclease-mediated targeted integration. The factors may be introduced at any concentration that is sufficient to affect overall stem cell proliferation or affect the particular stem cell sub population. In certain embodiments, the factors are introduced into the culture medium, for example at a concentration of between 0.1 nM and 100 µM (or any value therebetween).

In one aspect, described herein is a method for increasing gene modification (e.g., deletions and/or additions) in a stem cell by culturing the cell in the presence of one or more factors that affect and/or increase stem cell expansion without loss of stemness (e.g., a histone deactylase inhibitor (HDACI) such as valproic acid (VPA)) before, during, and/or after administration of an exogenous nuclease (wherein the exogenous nuclease mediates cleavage and/or modification of a cell's genome. The increase in gene modification is as compared to a cell population not cultured in the presence of the one or more factors. In certain embodiments, the factor is a HDACI such as VPA. Optionally, lithium chloride (Li) may be included in the culture medium. In certain embodiments, the methods further comprise the steps of: introducing one or more nucleases (and/or expression constructs or mRNAs that encode and express the nuclease(s)) into a host cell, thereby increasing nuclease-mediated gene disruption in the cell. In certain embodiments, the factor(s) (e.g., VPA or VPA plus Li) is (are) introduced before, during, and/or after introduction of the nucleases. In still further embodiments, the methods further comprise introducing one or more exogenous sequences (e.g., donors) into the cell before, during and/or after introduction of the nuclease(s) such that the donor molecule is introduced into the genome of the cell following cleavage by the nuclease(s) via homology-dependent or homology-independent mechanisms.

The factor(s) (e.g., one or more HDACI such as VPA) may be introduced at any concentration that is sufficient to affect stem cell proliferation and/or genomic modification for the particular stem cell population. In certain embodiments, the factor (e.g., VPA) is introduced into the culture medium, for example at a concentration of between 0.1 nM and 100 mM (or any value therebetween), including between 1 and 5 mM (or any value therebetween) in certain embodiments, preferably below 3 mM. Lithium chloride may also be used any suitable concentration, including between 0.1 nM and 100 mM (or any value therebetween), including between 1 and 5 mM (or any value therebetween) in certain embodiments, preferably at least 5 mM.

Furthermore, in any of the methods described herein, VPA may be introduced in to the cell culture before, during and/or after addition of the nuclease(s) and/or donors. In certain embodiments, VPA is administered before the nucleases and/or donors (which donors and nucleases may be administered sequentially in any order and/or concurrently). In other embodiments, VPA is administered with the nucleases and/or donors. In still further embodiments, VPA is administered multiple times, for example, before and after the nucleases and/or donors. In still further embodiments, VPA is administered before nuclease administration and after donor administration or alternatively, before donor administration and after nuclease administration. In addition, VPA may be added to the cell culture for any period of time prior to nuclease(s) and/or donor(s).

In some embodiments, the nuclease which facilitates genomic engineering of the cell is delivered as a peptide, while in others it is delivered as a nucleic acid encoding the nuclease. In some embodiments, more than one nuclease is used and may be delivered in nucleic acid form, protein form, or combinations thereof. In some preferred embodiments, the nucleic acid(s) encoding the nuclease is(are) an mRNA, and in some instances, the mRNA is protected. In further preferred embodiments, the mRNA may comprise an ARCA cap and/or may comprise a mixture of modified and unmodified nucleotides. The nuclease may comprise a zinc finger nuclease (ZFN), a TALE-nuclease (TALEN), TtAgo, or a CRISPR/Cas nuclease system or a combination thereof. In a preferred embodiment, the nucleic acid encoding the nuclease(s) is delivered via electroporation. In other embodiments, the nucleic acid encoding the nuclease(s) is delivered via a lipid nanoparticle (LNP).

In another aspect, described herein is a method for increasing targeted integration (e.g., via HDR) following nuclease-mediated cleavage in a cell. In certain embodiments, the methods comprise the steps of: (i) introducing one or more nucleases (and/or mRNAs or expression constructs that express the nuclease(s) and one or more single guide RNA if needed) along with one or more donor molecules into a host cell and (ii) introducing one or more factors that affect and/or increase stem cell expansion without loss of stemness or an induction of differentiation in the cell (e.g., VPA) to the culture media containing the cell before, during and/or after introduction of the nuclease(s). The donor may be delivered prior to, after, or along with the nucleic acid encoding the nuclease(s). In certain embodiments, the donor molecule comprises a sequence selected from the group consisting of a sequence (e.g., gene) encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

In some embodiments, the donor comprises a full length gene flanked by regions of homology with the targeted cleavage site. In some embodiments, the donor lacks homologous regions and is integrated into a target locus through homology independent mechanism (i.e. NHEJ-mediated end capture). In other embodiments, the donor comprises a smaller piece of nucleic acid flanked by homologous regions for use in the cell (i.e. for gene correction). In some embodiments, the donor comprises a gene encoding a functional or structural component such as a shRNA, RNAi, miRNA or the like. In other embodiments the donor comprises a gene encoding a regulatory element that binds to and/or modulates expression of a gene of interest. In other embodiments, the donor is a regulatory protein of interest (e.g. ZFP TFs, TALE TFs or a CRISPR/Cas TF) that binds to and/or modulates expression of a gene of interest. In one embodiment, the regulatory proteins bind to a DNA sequence and prevent binding of other regulatory factors. In another embodiment, the binding of the regulatory protein may modulate (i.e. induce or repress) expression of a target DNA. In certain embodiments, the nucleic acid sequence comprises a sequence encoding an antibody, an antigen, an enzyme, a growth factor, a receptor (cell surface or nuclear), a hormone, a lymphokine, a cytokine, a reporter, functional fragments of any of the above and combinations of the above. In embodiments in which the functional polypeptide encoding sequences are promoterless, expression of the integrated sequence is then ensured by transcription driven by an endogenous promoter or other control element in the region of interest. In other embodiments, a "tandem" cassette is integrated into the selected site in this manner, the first component of the cassette comprising a promoterless sequence as described above, followed by a transcription termination sequence, and a second sequence, encoding an autonomous expression cassette. Additional sequences (coding or non-coding sequences) may be included in the donor molecule between the homology arms, including but not limited to, sequences encoding a 2A peptide, SA site, IRES, etc. In some embodiments, the donor molecule may comprise one or more sequences encoding a functional polypeptide (e.g., a cDNA), with or without a promoter.

The donor can be delivered by viral and/or non-viral gene transfer methods. In certain embodiments, the donor is delivered to the cell via an adeno associated virus (AAV). In some instances, the AAV comprises LTRs that are of a heterologous serotype in comparison with the capsid serotype. In other embodiments, the donor is delivered to the cell via a lentivirus. In some instances, the lentivirus is an integrase defective lentivirus (IDLV). In other embodiments, the donor is delivered to the cell via an LNP.

In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN). In yet further embodiments, the DSB is created using a CRISPR/Cas nuclease system where an engineered single guide RNA or its functional equivalent is used to guide the nuclease to a targeted site in a genome. In yet further embodiments, the DSB is created using a TtAgo system. In another aspect, the invention provides a host cell, including a cell culture, comprising one or more nucleases (and/or a polynucleotide encoding one or more nucleases) and/or the TtAgo or CRISPR/Cas nuclease system and one or more factors that affect stem cell expansion without loss of stemness and/or induction of differentiation in the cell (e.g., a HDACI such as VPA and/or Li)) in the surrounding culture medium. In certain embodiments, the invention provides a cell culture comprising: a stem cell comprising an exogenous nuclease; and a histone deactylase inhibitor (HDACI), both in a culture medium. In certain embodiments, the cell culture further comprises a donor sequence. In certain embodiments, the cell is a eukaryotic cell (e.g., a mammalian or plant cell). In some aspects, the host cell further comprises a donor DNA. In some aspects, the host cells are an established cell line while in other aspects, the host cell is a primary cell isolated from a mammal. The nuclease(s) may be, for example, zinc finger nucleases (ZFNs), TAL-effector domain nucleases (TALENs), homing endonucleases, a TtAgo system and/or an engineered nuclease system comprising engineered single guide RNAs and the CRISPR/Cas nuclease. In some aspects, the donor DNA encodes a polypeptide, a regulatory region, or a structural nucleic acid. Also, described are cells or cell lines descended from the host cell (or cell cultures) as described herein, including genetically modified stem cells or their descendants which may or may not include the exogenous nuclease(s) but which include one or more nuclease-mediated genetic modifications.

In yet another aspect, provided herein is a genetically modified stem cell (e.g., hematopoietic stem cell). In certain embodiments, the stem cell is made by the methods described herein and/or descended from the host cells or cell cultures as described herein. In other embodiments, provided herein is a population of modified stem cells. In preferred embodiments, provided is a long term sub population of modified stem cells (LT-HSC). Any of the stem cells described herein, may comprise a nuclease-inactivated gene or genes and/or one or more donor molecules integrated via targeted insertion using a nuclease. In certain embodiments, the genetically modified stem cells as described do not include any viral vector sequences integrated into the genome.

In another aspect, the invention provides kits that are useful for increasing gene disruption and/or targeted integration following nuclease-mediated cleavage of a cell's genome, particularly in an HSC (e.g. ZFNs, TAL-effector domain nuclease fusion proteins, a TtAgo system, or engineered homing endonucleases or engineered guide RNAs with the CRISPR/Cas system). The kits typically include one or more nucleases that bind to a target site, one or more factors that affect stem cell expansion and/or differentiation (e.g., VPA or VPA plus Li) and instructions for introducing the nucleases and stem cell-affecting factors into the cells such that nuclease-mediated gene disruption and/or targeted integration is enhanced. Optionally, cells containing the target site(s) of the nuclease may also be included in the kits described herein. In certain embodiments, the kits comprise at least one construct with the target gene and a known nuclease capable of cleaving within the target gene. Such kits are useful for optimization of cleavage conditions in a variety of varying host cell types. Other kits contemplated by the invention may include a known nuclease capable of cleaving within a known target locus within a genome, and may additionally comprise a donor nucleic acid. In some aspects, the donor DNA may encode a polypeptide, a regulatory region or a structural nucleic acid. In some embodiments, the polypeptide is a reporter gene (e.g. GFP or GUS). Such kits are useful for optimization of conditions for donor integration or for the construction of specifically modified cells, cell cultures, cell lines, and transgenic plants and animals containing gene disruptions or targeted insertions.

In other aspects, methods of administering a genetically modified cell (e.g., stem cell) or population of genetically modified cells (e.g., stem cells or a subpopulation of LT-HSC) as described herein to a subject are described (e.g., ex vivo methods). The genetically modified stem or precursor cells (e.g., "HSC/PC") as described herein are typically given in a bone marrow transplant and the HSC/PC differentiate and mature in vivo. In some embodiments, the genetically modified HSC/PC are isolated following G-CSF or plerixafor-induced mobilization, and in others, the cells are isolated from human bone marrow or umbilical cords. The genetically modified cells administered may be produced on a large scale, for example involving pre-stimulation. In some embodiments, the genetically modified cells are stimulated after modification for large scale expansion. Administration of the cells may be by any suitable method, including injection, inhalation, transfection (e.g., via any high capacity system transfection system) or the like. In some aspects, the HSC/PC are edited by treatment with a nuclease designed to knock out a specific gene or regulatory sequence. In other aspects, the HSC/PC are modified with an engineered nuclease and a donor nucleic acid such that a wild type gene or other gene of interest is inserted and expressed and/or an endogenous aberrant gene is corrected. In some embodiments, the modified HSCs/PC are administered to the subject (e.g., patient) following mild myeloablative pre-conditioning. In other aspects, the HSC/PC are administered after full myeloablation such that following engraftment, 100% of the hematopoietic cells are derived from the modified HSC/PC. Furthermore, the cell may be arrested in the G2 phase of the cell cycle.

In some embodiments, the transgenic HSC/PC cell, LT-HSC and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

These and other aspects will be readily apparent to the skilled artisan in light of disclosure as a whole.

BRIEF DESCRIPTION OF THE DRAWINGS

FIGS. 1A through 1F depict genomic modification of HSCs. FIG. 1A is a schematic showing the experimental timeline. FIG. 1B is a graph showing genomic modifications ("TI" refers to targeted integration of an exogenous donor molecule and "indels" refers to insertions and/or deletions following NHEJ) in the indicated cells types. FIG. 1C is a graph showing the percent of the indicated cells that express GFP, indicative or TI of the GFP reporter. FIG. 1D is a graph showing relative intracellular levels (normalized) of an AAV donor (IL2RG or SA2AGFP) in the indicated cell type. FIG. 1E is a graph showing levels of ZFN mRNA (normalized) in the indicated cell type. FIG. 1F is a graph showing the percent genomic modification in the indicated cells. The left bar of each pair shows indels and the right bar of each pair shows modification by targeted integration of the indicated donor.

FIG. 2A depicts the percent of CD90+ cells in cultures with the indicated substance (Control cell data is indicated by large space dashed line; nicotinamide—dotted line; TEPA—closer dashes line; VPA—solid line). FIG. 2B depicts the percent of cell viability in cultures with of the indicated substance (line identities same as for 2A). FIG. 2C depicts results of methylcellulose assays on CD34+ cell cultures comprising the indicated substances. The left most bar of each group shows colony forming units (erythroid) (CFU-E); the middle bar in each group shows colony forming units (granulocyte, monocyte) (CFU-GM); and the right bar of each group shows pluripotent colony forming units (granulocyte, erythrocyte, monocyte, megakaryocyte) (CFU-GEMM).

FIGS. 3A through 3H are graphs showing various effects of VPA, dmPEGE2 or SR1 on HSCs. FIG. 3A depicts the percent of CD90+ cells in cultures with indicated substance (Control cell data is indicated by large space dashed line; VPA-dotted line; dmPEGE2—closer dashes line; SR1—solid line. These line identities as used for FIGS. 3A-3F). FIG. 3B depicts the percent of CD133+ cells in cultures with indicated substance. FIG. 3C depicts the percent of CD49f+ cells in cultures with the indicated substance. FIG. 3D depicts the percent of CD34+ cells in cultures with the indicated substance. FIG. 3E depicts cell viability in cultures with the indicated substance. FIG. 3F depicts cell density following treatment with the indicated substance. FIG. 3G depicts results of methylcellulose assays on CD34+ cell cultures comprising the indicated substances. The left most bar of each group shows colony forming units (erythroid) (CFU-E); the bar second from the left in each group shows burst forming erythroid units (BFU-E); the bar second from the right shows colony forming units (granulocyte, monocyte) (CFU-GM); and the right most bar of each group shows pluripotent colony forming units (granulocyte, erythrocyte, monocyte, megakaryocyte) (CFU-GEMM). FIG. 3H depicts results of methylcellulose assays on CD34+ cell cultures comprising the indicated substances. The left most bar of each group shows colony forming units (erythroid) (CFU-E); the middle bar in each group shows colony forming units (granulocyte, monocyte) (CFU-GM); and the right bar of each group shows pluripotent colony forming units (granulocyte, erythrocyte, monocyte, megakaryocyte) (CFU-GEMM).

FIGS. 4A through 4F are graphs depicting cell characterization and genomic modification of VPA-treated cells. FIG. 4A shows the % of the indicated cell types (by cell surface marker). The left bar shows the percentages in untreated cells (dark gray). The middle bar shows the percentages in cells cultured with VPA (light gray). The right bar shows the percentages in cells cultures with VPA and lithium chloride ("VPA+Li", medium gray). FIG. 4B shows the percentage of the indicated cell types at day 7 of culture under the indicated conditions. The left bar shows results of untreated cells. The middle bar shows results of cells treated with VPA and the right bar shows results of cells treated with VPA and lithium (VPA+Li). FIG. 4C is a graph depicting genomic modification in the indicated cell types via targeted integration of an SA-2A-GFP donor in mPB HSCs. FIG. 4D is a graph depicting genomic modification in the indicated cell types via targeted integration of a GFP donor in bone marrow aspirates (bm) HSCs. For FIGS. 4C and 4D, the left most bar in each group (control or VPA+Li) shows GFP expression in CD34+ cells; the bar second from the left in each group shows GFP expression in CD133+ cells; the middle bar of each group shows GFP expression in CD90+ cells; the bar second from the right in each group shows GFP expression in CD49f+ cells and the right-most bar of each group shows GFP expression in all cells ("total"). FIGS. 4E and 4F are graphs depicting the percent genomic modification in the indicated cell types. The left bar of each group shows modifications via NHEJ and the right bar of each group shows modifications by targeted integration ("TI").

FIGS. 5A through 5E are graphs showing various effects of VPA on nuclease plus IL2RG cDNA template donor-modified ("modified") and unmodified ("unmodified") HSCs. FIG. 5A depicts the percent of CD90+ cells. FIG. 5B depicts the percent of CD34+ cells. FIG. 5C depicts the percent of CD133+ cells. FIG. 3D depicts the percent of CD49f+ cells. FIG. 5E depicts cell viability.

FIGS. 6A through 6H are graphs showing various effects of VPA on nuclease plus IL2RG cDNA template donor-modified ("modified") and unmodified ("unmodified") HSCs. FIG. 6A depicts the percent of CD90+ cells. FIG. 6B depicts the percent of CD133+ cells. FIG. 6C depicts the percent of CD34+ cells. FIG. 6D depicts the percent of CD49f+ cells. FIG. 6E depicts cell viability. FIG. 6F depicts cell density. FIGS. 6G and 6H are graphs depicting the percent genomic modification (FIG. 6G) and relative genomic modification (FIG. 6H) in the indicated cell types. The left bar of each group shows modifications via NHEJ and the right bar of each group shows modifications by targeted integration ("TI").

DETAILED DESCRIPTION

Figure 1D:
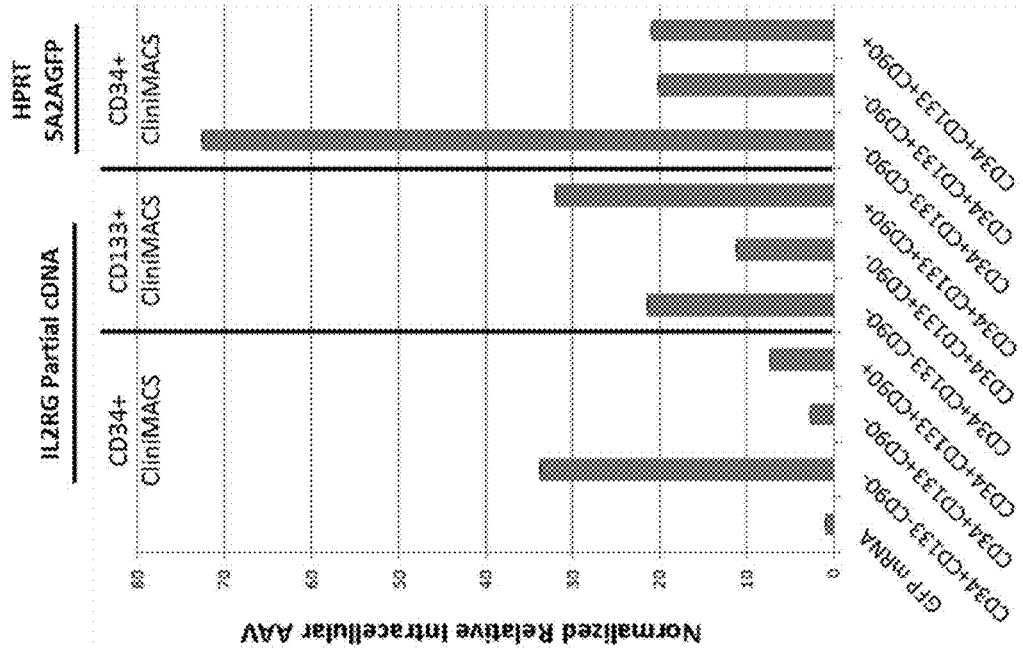

Disclosed herein are compositions and methods for transduction of a cell for use in gene therapy or genome engineering. In particular, nuclease-mediated (i.e. ZFN, TALEN, TtAgo or CRISPR/Cas system) targeted integration of an exogenous sequence or genome alteration by targeted cleavage followed by non-homologous end joining, is efficiently achieved in a cell. Particularly useful for transduction and engineering of HSC/PC, the methods and compositions can also be used for other cell types. In addition, described are methods and compositions for genome editing of a sub-population of CD34+ stem cells that are long-term human stem cells (LT-HSC). The methods and compositions provided here are useful to increase the overall percentage of edited stem cells and/or LT-HSC in a population of stem cells. Editing of this LT-HSC population is particularly useful to preserve the edited profile in a population of stem cells. Also described are methods and compositions for genome editing in large scale processes for use in cell-based gene therapies.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,585,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g. Swarts et al, ibid, G. Sheng et al., (2013) *Proc. Natl. Acad. Sci. U.S.A.* 111, 652). A "TtAgo system" is all the components required including e.g. guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, TALENs, TtAgo or CRIPSR/Cas systems can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 20080131962 and 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween). The donor sequence may encode a polypeptide (e.g., a polypeptide lacking or deficient in a disorder), a chimeric antigen receptor (CAR), and/or may include RNA sequences such as antisense RNAs, RNAi, shRNAs and/or micro RNAs (miRNAs).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylates, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE, TtAgo or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE, TtAgo or Cas DNA-binding domain is fused to an activation domain, the ZFP, TALE, TtAgo or Cas DNA-binding domain and the activation domain are in operative linkage if, in the fusion polypeptide, the ZFP, TALE, TtAgo or Cas DNA-binding domain portion is able to bind its target site and/or its binding site, while the activation domain is able to upregulate gene expression. When a fusion polypeptide in which a ZFP, TALE, TtAgo or Cas DNA-binding domain is fused to a cleavage domain, the ZFP, TALE, TtAgo or CasDNA-binding domain and the cleavage domain are in operative linkage if, in the fusion polypeptide, the ZFP, TALE, TtAgo or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a disorder.

"Stemness" refers to the relative ability of any cell to act in a stem cell-like manner, i.e., the degree of toti-, pluri-, or oligo-potency and expanded or indefinite self-renewal that any particular stem cell may have.

Factors that Enhance Genomic Modification of Stem Cells

Any factor or factors that enhance(s) genomic modification of stem cells can be used in the practice of the present invention. The factors may be introduced directly into the cell (for example, as genes encoding the factor(s)) and/or may be are introduced into the culture medium (including feeder layers and other solid substrates). The use of such factors, for example in the culture conditions before, during or after nuclease-mediated genome modification is induced, increases the rate of nuclease-mediated modification of the stem cell.

Non-limiting examples of factors that can be used in the present invention include dimethyl prostaglandin E2 (PGE2) (Cutler et al. (2013) *Blood* 122(17):3074-81), tetraethylenepentamine (TEPA) (de Lima et al. (2008) *Bone Marrow Transplantation* 41(9):771-8), nicotinamide (Horwitz et al. (2014) *J Clinical Investigation* 124(7): 3121-3128), StemRegenin 1 (SR1), UM729 and UM171 (Fares et al. (2014) *Science* 345(6203):1509-1512), rapamycin (see Wang et at (2014) Blood. pii: blood-2013-12-546218), angiopoietin-like proteins ("Angptls", e.g. Notch/delta/ANGPTL5 (see Zhang et at (2008) *Blood.* 111(7):3415-3423), Angptl2, Angptl3, Angptl5, Angptl7, and Mfap4), IGF-binding protein 2 (IGFBP2), nicotinamide (see Horwitz et at (2014) *J. Clin. Invest* 124:3121-3128), Tat-myc (see WO2010025421) and tat-Bcl2 (see WO2014015312) fusion proteins, MAPK14/p38a Ly2228820 (see Baudet et at (2012) *Blood* 119(26):6255-6258), products of self-renewing genes such as HOXB4, OCT3/4 cord blood and/or MSC derived feeder layers or an ex vivo vascular niche co-culture system termed E4+EC (see Butler et al (2012) *Blood.* 120(6): 1344-1347), cytokines, (by way of non-limiting example Stemspan™ CC110, CC100, and/or H3000 (Stemcell™ technologies), Flt-3 ligand, SCF, TPO) and epigenetic modifiers such as valproic acid (VPA) (Chaurasia et al. (2014) *J Clinical Investigation* 124(6):2378-95; Walasek et al. (2012) *Blood* 119(13):3050-9), In some embodiments, the factors comprise StemRegenin (SR1, see, e.g., U.S. Pat. No. 8,741,640; Boitano et al, (2010) *Science* 329(5997):1345-1348), an aryl hydrocarbon receptor (AhR) antagonist that promotes expansion of CD34+ cells ex vivo is used in the methods and compositions described herein. In other embodiments, the factors comprise UM171 (see Fares et at (2013) *Blood:* 122 (21)), which is an agonist of stem cell renewal. In still other aspects, the factor comprises one or more prostaglandins, for example, dmPGE2. See, e.g., U.S. Pat. No. 8,168,428; North et at (2007) *Nature* 447(7147): 1007-1011). In some aspects, the factor comprises one or more hormones such as angiopoietin-like proteins ("Angptls", e.g. Angptl2, Angptl3, Angptl5, Angptl7, and Mfap4) and IGF-binding protein 2 (IGFBP2) are used. See, e.g., U.S. Pat. No. 7,807,464; Zhang et al (2008) 111(7): 3415-3423). In other aspects, the factors comprise one or more protein products of self-renewing genes such as HOXB4 or OCT are used. See, e.g., U.S. Pat. No. 8,735,153; Watts et at (2012) *Exp Hematol.* 40(3): 187-196). Alternatively these genes may be transiently expressed in the culture medium and/or in the stem cells.

The factors that affect stem cell expansion may be also comprise cellular support methods, including but not limited to feeder layers derived from stromal cell and/or MSC derived cells. See, e.g., Breems et at (1998) *Blood* 91(1): 111-117 and Magin et al., (2009) *Stem Cells Dev.* 2009 January-February; 18(1):173-86.

In certain embodiments, the factor comprises VPA and optionally lithium chloride (Li).

Any suitable amount of one or more factors may be used, so long as it is effective to increase nuclease activity and nuclease-mediated genomic modification. The particular concentrations used can be readily determined by one of skill in the art. Thus, nanomolar, micromolar or millimolar concentrations may be used as appropriate. In certain embodiments, millimolar concentrations of the one or more factors (e.g., VPA or VPA plus lithium chloride) are used, for example between 0.1 and 100 mM (or any value therebetween), preferably between 0.5 and 25 mM (or any value therebetween) and even more preferably between 1 and 5 mM concentrations (or any value therebetween).

Fusion Molecules

Described herein are compositions, for example nucleases, that are useful for cleavage of a selected target gene in a cell, particularly a stem cell. In certain embodiments, one or more components of the fusion molecules (e.g., nucleases) are naturally occurring. In other embodiments, one or more of the components of the fusion molecules (e.g., nucleases) are non-naturally occurring, i.e., engineered in the DNA-binding domain(s) and/or cleavage domain(s). For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS 1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch et at (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN). See, e.g., U.S. Pat. No. 8,586,526; Christian et at ((2010)<*Genetics epub* 10.1534/genetics. 110.120717). In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system. See, e.g., U.S. Pat. No. 8,697,359 and U.S. Patent Publication No. 20150056705, The CRISPR (clustered regularly interspaced short palindromic repeats) locus, which encodes RNA components of the system, and the cas (CRISPR-associated) locus, which encodes proteins (Jansen et al., 2002. *Mol. Microbial.* 43: 1565-1575; Makarova et al., 2002. *Nucleic Acids Res.* 30: 482-496; Makarova et al., 2006. *Biol. Direct* 1:7; Haft et al., 2005. *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celcius. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity, including for use in genome modification in a variety of organisms. See, for example, United States Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95:10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example. in U.S. Patent Publication Nos, 20050064474; 20060188987; 20090305346 and 20080131962, the disclosures of all of which are incorporated by reference in their entireties herein. Amino acid residues, at positions 446, 447, 479, 483, 484, 486, 487, 490, 491, 496, 498, 499, 500, 531, 534, 537, and 538 of FokI are all targets for influencing dimerization of the FokI cleavage half-domains.

Cleavage domains with more than one mutation may be used, for example mutations at positions 490 (E→K) and 538 (I→K) in one cleavage half-domain to produce an engineered cleavage half-domain designated "E490K: I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey'" mutations (see Guo et al, (2010) *J. Mol. Biol.* 400(1):96-107).

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek et al. (2012) *Science* 17; 337(6096):816-21 and Cong, ibid).

Target Sites

As described in detail above, DNA-binding domains can be engineered to bind to any sequence of choice. An engineered DNA-binding domain can have a novel binding specificity, compared to a naturally-occurring DNA-binding domain.

Non-limiting examples of suitable target genes a beta (β) globin gene (HBB), a gamma (δ) globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, a Rag-1 gene, an RFX5 gene, a FAD2 gene, a FAD3 gene, a ZP15 gene, a KASII gene, a MDH gene, and/or an EPSPS gene.

In certain embodiments, the nuclease targets a "safe harbor" loci such as the AAVS1, HPRT, albumin and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 20100218264; 20120017079; 20110265198; 20130137104; 20130122591; 20130177983 and 20130177960) and the Zp15 locus in plants (see U.S. Pat. No. 8,329,986).

Donors

In certain embodiments, the present disclosure relates to nuclease-mediated modification of the genome of a stem cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular chromatin. Further, for targeted insertion of sequences not normally present in a region of interest, said sequences can be present in a donor nucleic acid molecule and flanked by regions of homology to sequence in the region of interest.

As with nucleases, the donors can be introduced into any form. In certain embodiments, the donors are introduced in mRNA form to eliminate residual virus in the modified cells. In other embodiments, the donors may be introduced using DNA and/or viral vectors by methods known in the art. See, e.g., U.S. Patent Publication Nos. 20100047805 and 20110207221. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter. The donor molecule may be inserted into an endogenous gene such that all, some or none of the endogenous gene is expressed. Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface, nuclear and/or chimeric antigen receptors (CARs)), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the transgene may include, for example, wild-type genes to replace mutated endogenous sequences. For example, a wild-type (or other functional) gene sequence may be inserted into the genome of a stem cell in which the endogenous copy of the gene is mutated. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes). Exemplary splice acceptor site sequences are known to those of skill in the art and include, by way of example only, CTGACCTCTTCTCT-TCCTCCCACAG, (SEQ ID NO:1)(from the human HBB gene) and TTTCTCTCCACAG (SEQ ID NO:2) (from the human Immunoglobulin-gamma gene).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Cells

Thus, provided herein are genetically modified stem cells, for example stem cells comprising an inactivated gene and/or a transgene, including cells produced by the methods described herein. The transgene is integrated in a targeted manner into the cell's genome using one or more nucleases. Unlike random integration, targeted integration ensures that the transgene is integrated into a specified gene. The transgene may be integrated anywhere in the target gene. In certain embodiments, the transgene is integrated at or near the nuclease cleavage site, for example, within 1-300 (or any value therebetween) base pairs upstream or downstream of the site of cleavage, more preferably within 1-100 base pairs (or any value therebetween) of either side of the cleavage site, even more preferably within 1 to 50 base pairs (or any value therebetween) of either side of the cleavage site. In certain embodiments, the integrated sequence does not include any vector sequences (e.g., viral vector sequences).

Any cell type can be genetically modified as described herein to comprise a transgene, including but not limited to cells and cell lines. Other non-limiting examples of genetically modified cells as described herein include T-cells (e.g., CD4+, CD3+, CD8+, etc.); dendritic cells; B-cells; autologous (e.g., patient-derived). In certain embodiments, the cells are stem cells, including heterologous pluripotent, totipotent or multipotent stem cells (e.g., CD34+ cells, induced pluripotent stem cells (iPSCs), embryonic stem cells or the like). In certain embodiments, the cells as described herein are stem cells derived from patient.

The cells as described herein are useful in treating and/or preventing disorders in a subject with the disorder, for example, by ex vivo therapies. The nuclease-modified cells can be expanded and then reintroduced into the patient using standard techniques. See, e.g., Tebas et at (2014) *New Eng J Med* 370(10):901. In the case of stem cells, after infusion into the subject, in vivo differentiation of these precursors into cells expressing the functional protein (from the inserted donor) also occurs. Pharmaceutical compositions comprising the cells as described herein are also provided. In addition, the cells may be cryopreserved prior to administration to a patient.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to patients.

Methods of delivering nucleases as described herein are described, for example, in U.S. Pat. Nos. 6,453,242; 6,503, 717; 6,534,261; 6,599,692; 6,607,882; 6,689,558; 6,824, 978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933, 113; 6,979,539; 7,013,219; and 7,163,824, and U.S. Patent Publication No, 20140335063, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome, lipid nanoparticle (LNP), poly-lactate-glycolic acid nanoparticles, poly-amine complexing agents, or poloxamer. In some embodiments, the LNP are formulated for the in vivo deliver of mRNA (see for example PCT patent publication WO2013151736). Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989). Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al.,

*Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by an or AAV, while the one or more nucleases can be carried by mRNA. Furthermore, the different systems can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The disclosed compositions and methods can be used for any application in which it is desired to increase nuclease-mediated genomic modification in a stem cell, for example a hematopoietic (CD34+) stem cell for clinical cellular therapies. For example, the methods described herein will improve the therapeutic effect of ZFNs, TALENs, TtAgo and/or CRISPR/Cas systems in the following scenarios: ex vivo and in vivo gene disruption in CD34+ cells; ex vivo and in vivo gene correction of in CD34+ cells; and/or ex vivo and in vivo gene addition.

Kits

Also provided are kits for performing any of the above methods. The kits typically contain polynucleotides encoding one or more nucleases, one or more factors that affect stem cell expansion and/or donor polynucleotides as described herein as well as instructions for administering the factors that affect stem cells into the cells to which the nucleases and/or donor polynucleotide are introduced (or surrounding media). The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

The following Examples relate to exemplary embodiments of the present disclosure in which the nuclease comprises one or more ZFNs or one or more TALENs. It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains, mega TALs, compact TALENs and nuclease systems such as TtAgo and CRISPR/Cas using engineered single guide RNAs.

EXAMPLES

Example 1

Genome Modification of Primitive HSCs

Human mPB CD34+ or CD133+ cells were cultured ex vivo in CC110 (Stemcell Technologies) media for 3 days and underwent targeted integration (TI) of either (1) an SA-2A-GFP transgene (AAV donor) at HPRT intron 1 after a zinc-finger nuclease (ZFN) mRNA-mediated genome double-stranded break (SBS #s 34303/34306, described in U.S. Patent Publication Nos. 20130137104) or (2) an SA-IL2RG partial corrective cDNA transgene (AAV donor) at IL2RG intron 1 after a ZFN mRNA-mediated genome double-stranded break (SBS #s 44271/44298, as described in U.S. Provisional Application No. 62/030,942), both delivered by BTX electroporation in the timeline as shown in FIG. 1A.

As shown in FIG. 1B, Miseq next-generation sequencing (NGS) of cell populations sorted by FACS showed decreased ZFN-mediated NHEJ as well as HDR-driven TI in the more primitive cell populations (CD34+CD133+CD90− and CD34+CD133+CD90+) as well as in differentiated lineages (CD34−). FIG. 1C shows that expression of the SA-2A-GFP transgene was also decreased in the more primitive HSPCs as well as differentiated lineages (as assayed by flow cytometry).

Figure 1C:
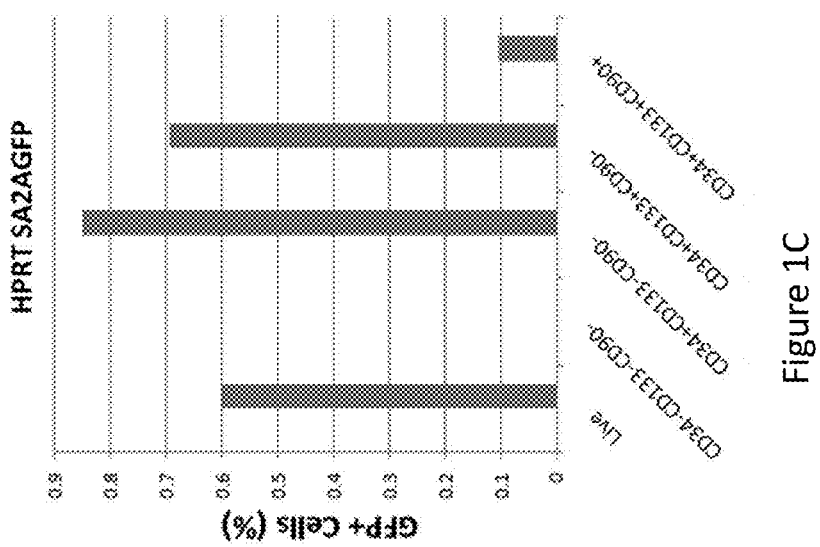

Genomic DNA (gDNA) was then harvested and qPCR was performed on a donor AAV-specific sequence, which showed fewer AAV episomes within more primitive cell populations (FIG. 1D). In addition, RNA from genome-modified cells was harvested and RT-PCR was performed before subsequent qPCR and showed less ZFN mRNA present in more primitive cells (FIG. 1E). Protein from genome-modified cells was harvested and Western blotting was performed and showed less ZFN protein present in more primitive cells. Less GFP expression was also observed in the most primitive cell population in cells modified at the HPRT locus (as assayed by flow cytometry). Furthermore, next generation sequencing (NGS) was performed and similar levels of ZFN-mediated NHEJ across HSPC cell populations, but less TI in the most primitive cells (FIG. 1F).

These data confirm that more primitive HSC populations are less amenable to genome modification (TI and/or NHEJ).

Example 2

Treatment of HSCs

A. VPA, Nicotinamide and TEPA

Human mPB CD34+ cells were cultured ex vivo in CC110 media for 3 days with or without VPA, nicotinamide or TEPA. Various cell surface markers are enriched on CD34+ subpopulations that contain true LT-HSCs. Measurement of such cell surface markers can therefore be used as a proxy for the number of LT-HSCs in the culture. In particular, CD90, CD133, CD49f, CD38, and CD166 can be used to assay LT-HSC number (Notta et al. (2011) *Science* 333(6039):218-21; Chitteti et al. (2014) *Blood* 124(4):519-29), with the LT-HSCs generally residing in the CD90+CD133+CD49f+CD38-low CD166+ pool. Accordingly, cells were stained using fluorescently-tagged antibodies against the HSPC multipotency markers CD34 (PE-Cy7), CD133 (PE), CD90 (APC), and CD49f (PerCP) and analyzed by flow cytometry.

Figure 2A:
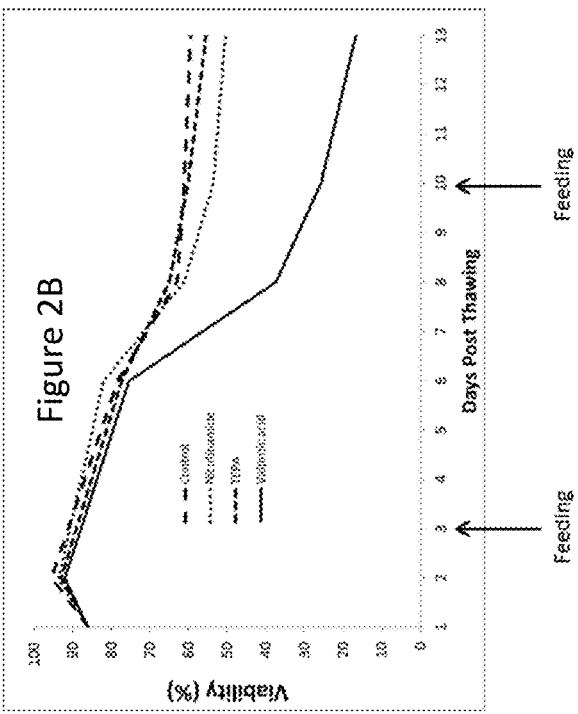
FIGS. 2A through 2C are graphs showing various effects of VPA, nicotinamide or TEPA on HSCs.
Figure 2C:
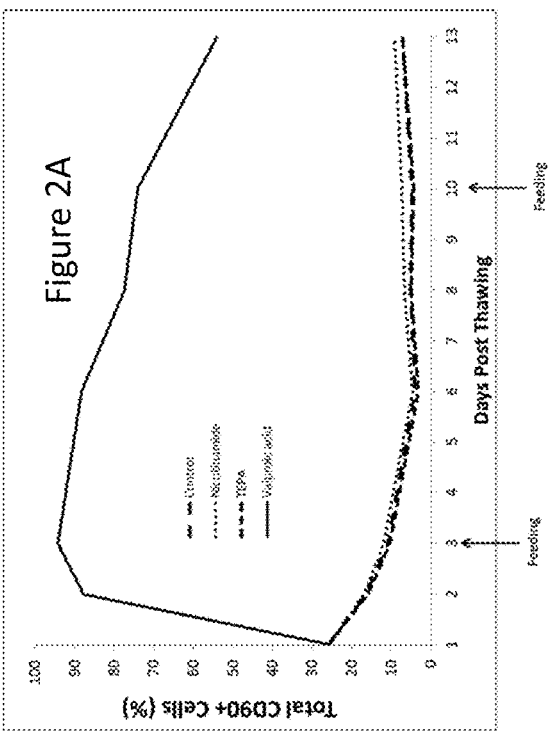
Figure 2B:
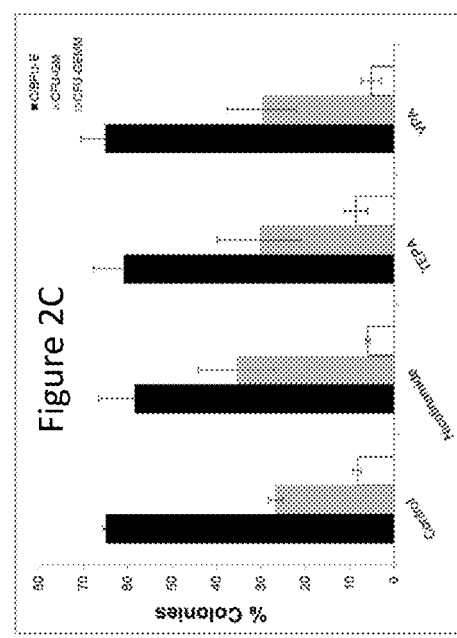

FACS analysis demonstrated that VPA (1.25 mM) increased the proportion of CD34+CD133+ cells, as well as the fraction of CD34+CD133+CD90+CD49f+ cells compared to controls (93.1% vs. 51.7% and 85.9% vs. 14.4%, respectively). FIG. 2A shows dramatically increased CD90 expression after VPA addition at 1 day post thawing, reaching a peak within 2 days before a gradual decline. No effect was seen with nicotinamide (2.5 mM) or TEPA (5 μM), other small molecules being tested in HSC-related clinical trials. FIG. 2B shows a decrease in cell viability after extended culture with VPA, and shows that the VPA associated viability decrease was very minimal before 6 days post thawing (as assayed by flow cytometry in the presence of propidium iodide). Furthermore, methylcellulose assays indicated no significant difference in myeloid or erythroid differentiation capacity with VPA compared to controls after 14 days of in vitro differentiation (FIG. 2C).

These results demonstrate that VPA increases HSC multipotency marker expression with little toxicity and that VPA treatment does not affect myeloid or erythroid differentiation.

B. VPA, dmPGE2 and SR1

Human mPB CD34+ cells were cultured ex vivo in CC110 media for 17 days. Cells were then stained using fluorescently-tagged antibodies against the HSPC multipotency markers CD34 (PE-Cy7), CD133 (PE), CD90 (APC), and CD49f (PerCP) and analyzed by flow cytometry as described above.

FACs analysis demonstrated that VPA (1.25 mM) dramatically increased CD90 expression after VPA addition at 1 day post thawing, reaching a peak within 2 days before a gradual decline (FIG. 3A). No effect was seen with 10 µM 16,16-dimethyl Prostaglandin E2 (dmPGE2) or 1 µM StemRegenin 1 (SR1). VPA also increased CD133 expression compared to controls, whereas SR1 resulted in decreased expression (FIG. 3B). In addition, VPA increased CD49f expression for up to 15 days compared to controls, whereas extended culture with SR1 resulted in increased expression compared to both controls and VPA after 17 days in culture (FIG. 3C). VPA and SR1 treated cells retained elevated CD34 expression compared to controls for the duration of the experiment, however SR1 results in higher expression with extended culture compared to VPA (FIG. 3D). FIG. 3E shows that there was no loss of cell viability after extended culture with VPA (potentially due to variation from human donor to donor), no effect on cell viability with dmPGE2 or SR1 (as assayed by flow cytometry in the presence of propidium iodide) and FIG. 3F shows that both dmPGE2 and SR1 resulted in a slight growth advantage of cells with extended culture, whereas VPA resulted in a slightly decreased proliferative capacity.

FIGS. 3G and 3H show results of methylcellulose assays and show no significant difference in myeloid or erythroid differentiation capacity with VPA compared to controls after 14 days of in vitro differentiation, whereas SR1 resulted in increased erythroid burst-forming units (BFU-E) as well as granulocyte and megakaryocyte colony-forming units (CFU-GM).

These results demonstrate that VPA increased HSC multipotency marker expression and did not affect myeloid or erythroid differentiation in vitro, whereas SR1 enhanced multipotency marker expression and colony forming potential with extended in vitro culture.

C. Additional Factors

CD34+ cells are cultured in the presence of one or more addition factors that affect stem cell expansion. One or more polynucleotides encoding one or more nucleases (ZFNs, TALENs, TtAgo, CRISPR/Cas) are introduced into CD34+ cells via suitable methods (e.g., electroporation for mRNA or plasmids). One or more factors that affect stem cell expansion are introduced into the cells and/or culture media before, during and/or after nuclease introduction. Control cells without such factors are also maintained.

Cells are harvested and genomic DNA prepared for Day 3 analysis by Surveyor™/Cell assay and DNA sequencing. For DNA sequencing the genomic target region of the ZFN is amplified by PCR, topo-cloned and individual clones are sequenced. Additionally, the regions flanking the cleavage site are sequenced using the MiSeq platform (Illumina). The sequences are analyzed and the results are used to divide the clones into groups by the genome type (e.g. wild type genomes, those with insertions and/or deletions, and those with other modifications such as targeted integration of any donor DNAs). At Day 3 harvest about a third of the cells were re-seeded in fresh medium without the factors that influence stem cell growth and were grown until day 10 when they were harvested and analyzed by Surveyor™/Cell assay.

The results show that CD34+ cell populations treated with one or more factors that affect stem cell expansion exhibit increased percentage of cells displaying nuclease-mediated cleavage, increased TI (as described below), and/or increased NHEJ (e.g., non-microhomology dependent NHEJ and/or microhomology dependent NHEJ).

Example 3

Effect on Nuclease-mediated Genomic Modification

A. VPA Addition Before Genomic Modification

Human mPB-derived cells were cultured as described above in the presence or absence of VPA (1.25 mM) and 5 mM lithium chloride (Li) and cells assayed for primitive cell surface markers as described above.

Figure 4A:
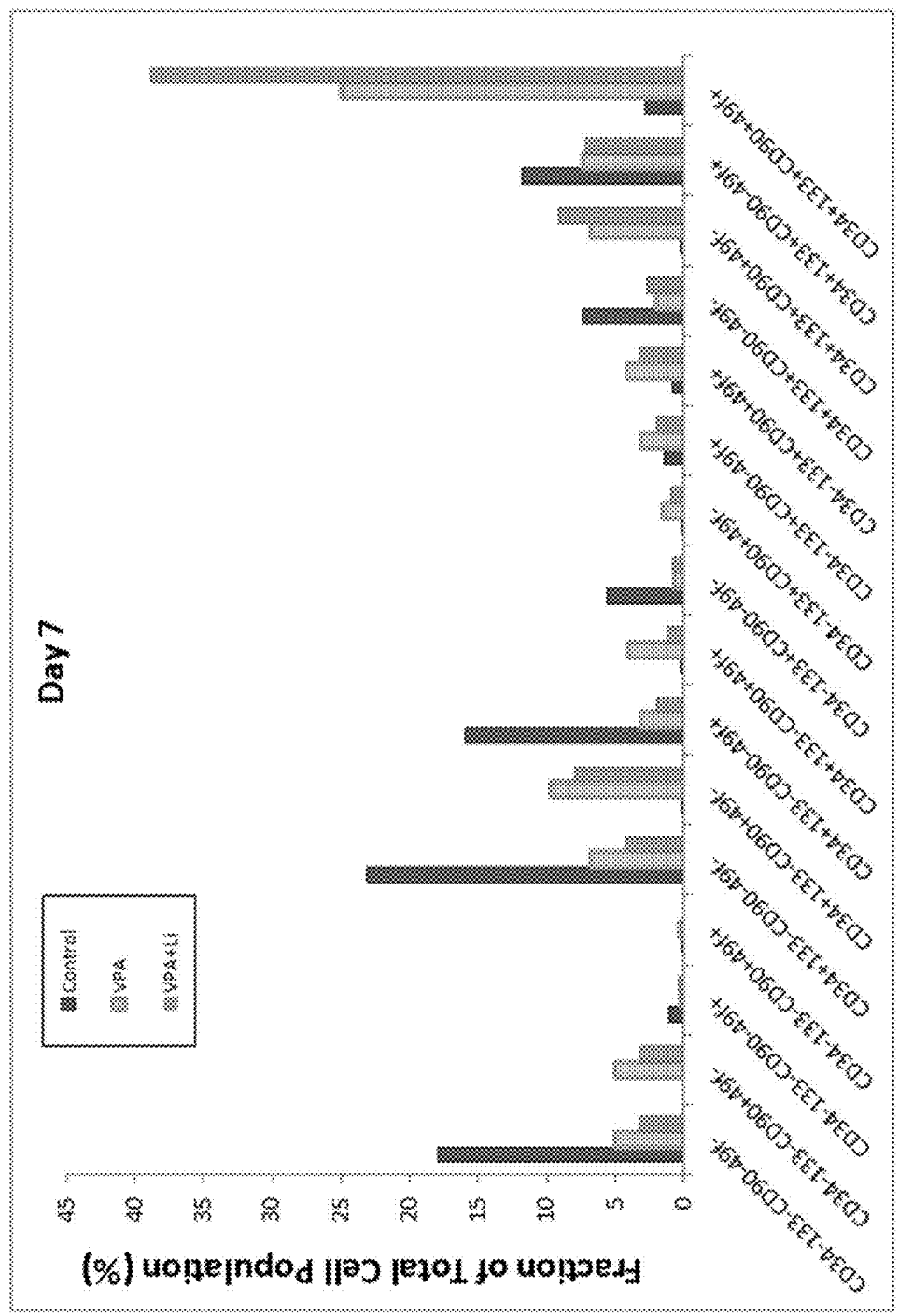

As shown in FIG. 4A, VPA and Li increased the fraction of the most primitive cell population (CD34+CD133+CD90+CD49f+) in cultured mPB-derived cells and decreased the fraction of the multipotency marker-negative populations compared to VPA alone and control after 7 days in culture and in the presence of VPA+Li for 6 days (as assayed by flow cytometry). FIG. 4B shows that lithium in addition to VPA increased the overall fraction of all of the HSPC multipotency markers analyzed compared to VPA alone and control in cultured mPB-derived cells after 7 days in culture and in the presence of VPA+Li for 6 days.

In addition, as shown in FIG. 4C, CD34+ cells were thawed and placed in appropriate culture conditions. After approximately one day in culture, VPA and Li were added to the culture media (same concentrations as above). After another approximately 12 hours, the cells were transfected with polynucleotides encoding exogenous (donor) sequences (e.g., AAV vectors). Subsequently, nucleases (mRNA encoding ZFNs) was added to the culture. In certain experiments, Human bone marrow (bm) aspirated CD34+ cells were cultured ex vivo in CC110 media and underwent targeted integration (TI) of an SA-2A-GFP transgene at HPRT intron 1 after a zinc-finger nuclease (ZFN)-mediated genome double-stranded break (SBS #s 34303/34306).

As shown in FIG. 4C, Human mPB CD34+ cells underwent targeted integration (TI) of an SA-2A-GFP transgene at the HPRT intron 1 after a zinc-finger nuclease (ZFN) mRNA-mediated genome double-stranded break (SBS #s 34303/34306) delivered by BTX electroporation. Cells exposed to VPA+Li expressed less GFP transgene than the controls. Less primitive cells (CD133+) showed higher GFP expression than more primitive cells (CD90+ and CD49f+).

In addition, as shown in FIG. 4D, human bone marrow (bm) aspirated CD34+ cells underwent targeted integration (TI) of an SA-2A-GFP transgene at HPRT intron 1 after a zinc-finger nuclease (ZFN)-mediated genome double-stranded break (SBS #s 34303/34306). Cells exposed to VPA+Li expressed less GFP transgene than controls.

Figure 4E:
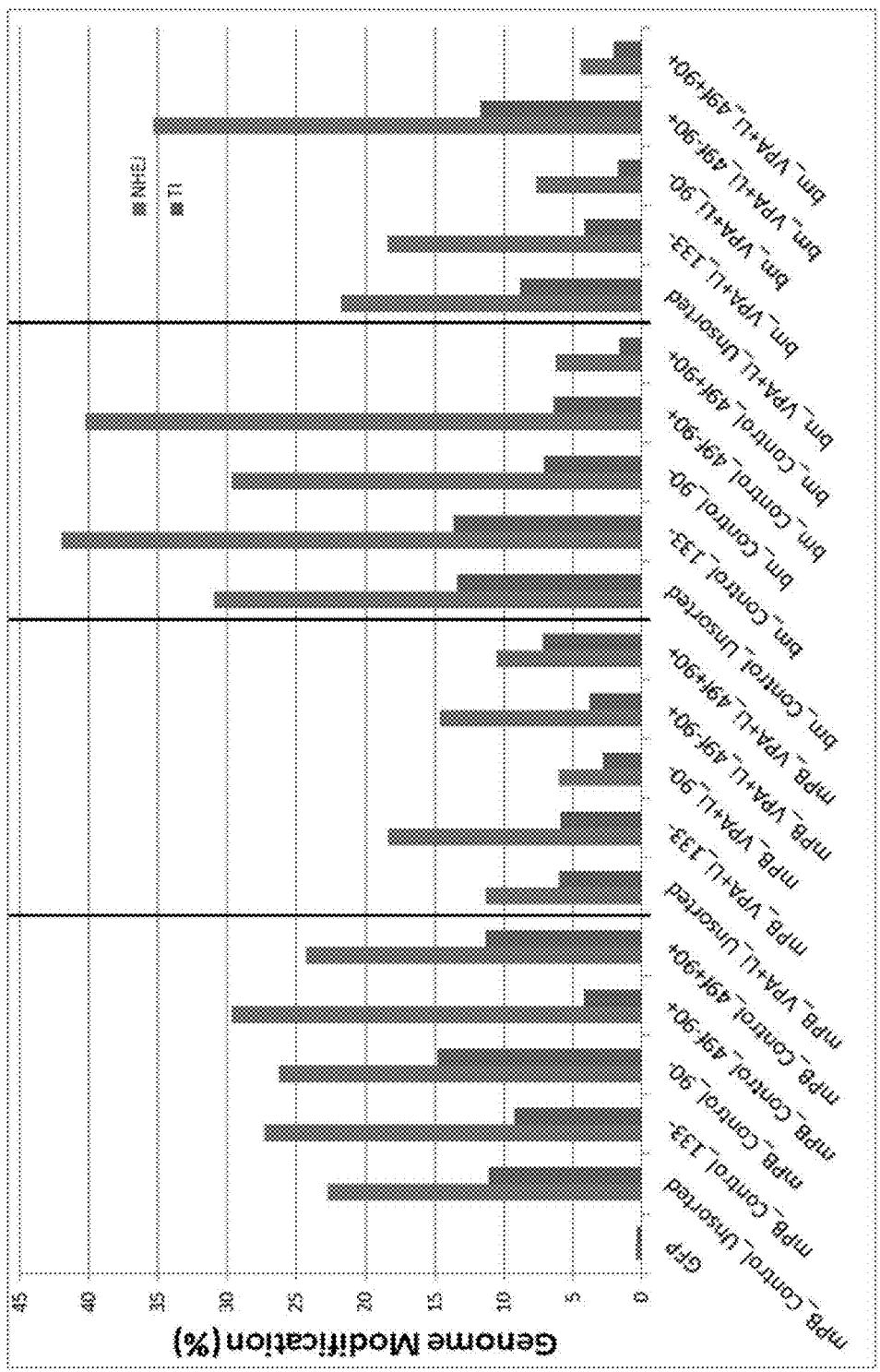
Figure 4F:
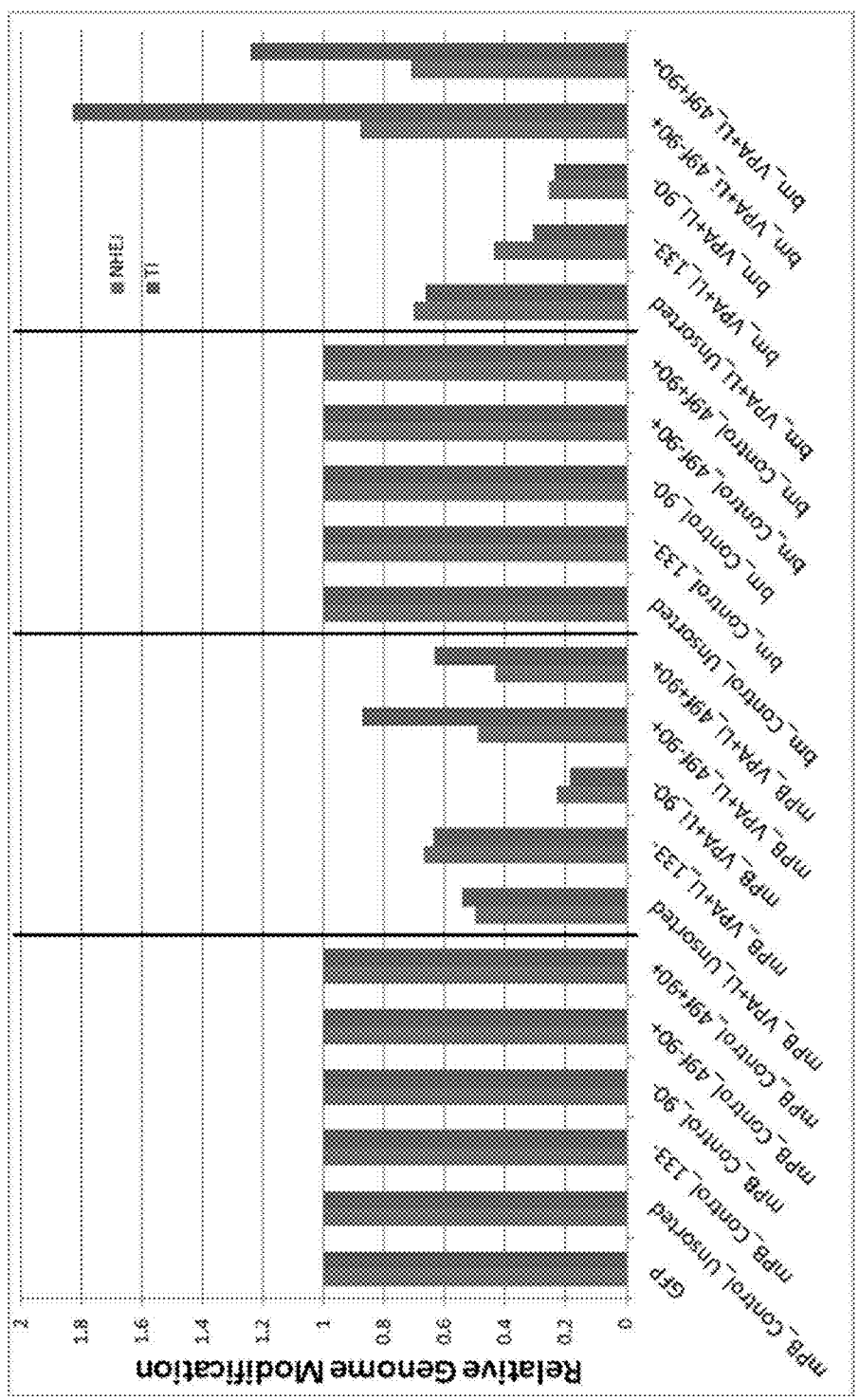

As shown in FIG. 4E, Miseq next-generation sequencing (NGS) of cell populations sorted by FACS showed an overall decrease in ZFN-mediated NHEJ as well as HDR-driven TI of the SA-2A-GFP transgene in cells exposed to VPA+Li compared to controls in both mPB and bm-derived cells. However, more TI was seen in the most primitive cell populations (CD90+) in bm-derived cells. Cells transfected with CMV-GFP mRNA were used as a negative control. FIG. 4F shows relative genome modification of VPA-exposed cells as compared to control cells.

These results demonstrate that VPA addition before genome modification lowered overall NHEJ and TI in both mPB and bm-derived HSPCs, but enhanced TI in the most primitive cell populations in bm-derived HSPCs.

B. VPA Addition after Extended Culture

CD34+ cells were cultured ex vivo in CC110 media with 100 ng/mL IL-6 for 8 days in the presence or absence of VPA, lithium, nucleases and donors. VPA and Li were added prior to nucleases and/or donors (which can be added in any order). Briefly, CD34+ cells were thawed and cultured for approximately one week before addition of VPA and Li and cultured again (e.g., 1-2 days) before addition of a donor. Nucleases (e.g., ZFN mRNA) were added 0.5 to 1 day later and VPA/Li washed out at the same time. After at least a day, cells were then stained using fluorescently-tagged antibodies against the HSPC multipotency markers CD34 (PE-Cy7), CD133 (PE), CD90 (APC), and CD49f (PerCP) and analyzed by flow cytometry.

FACs analysis showed that 5 mM Lithium chloride (Li) in addition to VPA (1.25 mM) increased the proportion of genome modified and unmodified CD34+CD133+ cells, as well as the fraction of CD90+ cells in both CD34+CD133+ and CD34+CD133− populations compared to controls even after extended culture. Notably, a distinct CD49f+ population was present with the CD34+CD133− group, which was not as present within the CD34+CD133+ group.

Figure 5D:
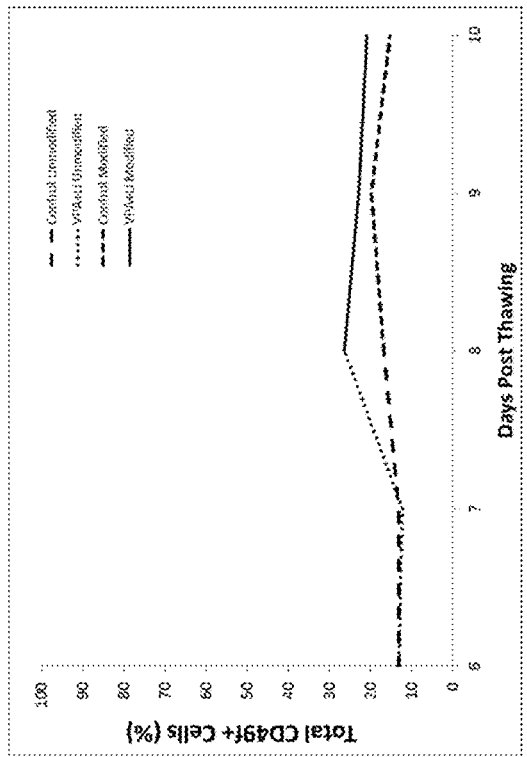
Figure 5E:
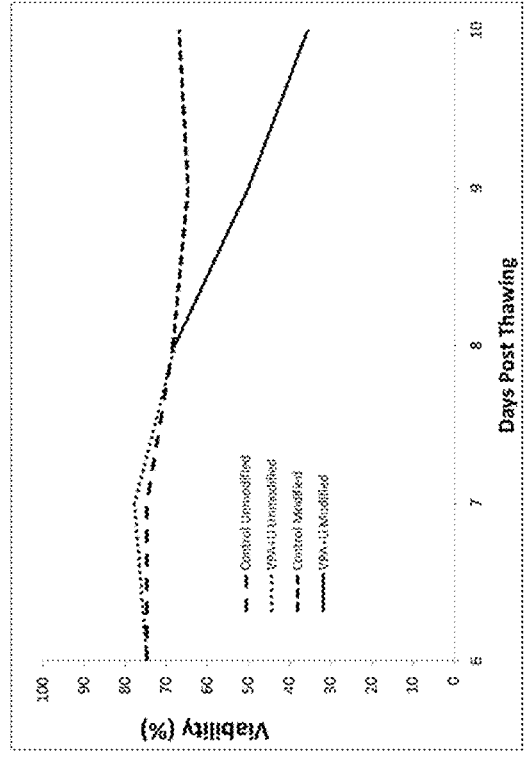

Furthermore, as shown in FIGS. 5A to 5D, VPA and Li increased CD90 expression (FIG. 5A), CD34 expression (FIG. 5B), CD133 expression (FIG. 5C) and CD49f expression (FIG. 5D) in both modified and unmodified cells. Cells retained high CD90, CD34, CD133 and CD49f expression after VPA washout and genome modification. In addition, as shown in FIG. 5E, no decrease in viability was seen after VPA addition compared to controls until after genome modification, wherein a significant viability loss was seen within 2 days in culture (as assayed by flow cytometry in the presence of propidium iodide).

These results demonstrated that VPA addition in mPB-derived HSPCs after extended culture enhanced multipotency, and washing out VPA after genome modification did not drastically reduce its effects.

C. VPA Addition after Genomic Modification

CD34+ cells were cultured ex vivo in CC110 media as described above for approximately 6 days in the presence or absence of VPA, lithium, nucleases and donors. VPA and Li were added after to nucleases and/or donors (which can be added in any order). Briefly, CD34+ cells were thawed and cultured for approximately 2-3 days before addition of a donor. Nucleases (e.g., ZFN mRNA) were added 0.5 to 1 day after transfection with the donor. The donor was a SA-IL2RG partial corrective cDNA transgene at IL2RG intron 1 and the zinc-finger nucleases (ZFN) were SBS #s 44271/44298 delivered by BTX electroporation. VPA/Li was added 1 day after addition of the ZFN mRNA. After approximately 3 days, cells were then stained using fluorescently-tagged antibodies against the HSPC multipotency markers CD34 (PE-Cy7), CD133 (PE), CD90 (APC), and CD49f (PerCP) and analyzed by flow cytometry.

FACs analysis showed that 5 mM Lithium chloride (Li) in addition to VPA (1.25 mM) increased the proportion of CD34+CD133+ cells, as well as the fraction of CD90+ cells in both CD34+CD133+ and CD34+CD133− populations compared to controls in genome modified cells. Again, a distinct CD49f+ population was present with the CD34+CD133− group, which is not as present within the CD34+CD133+ group.

Figure 6E:
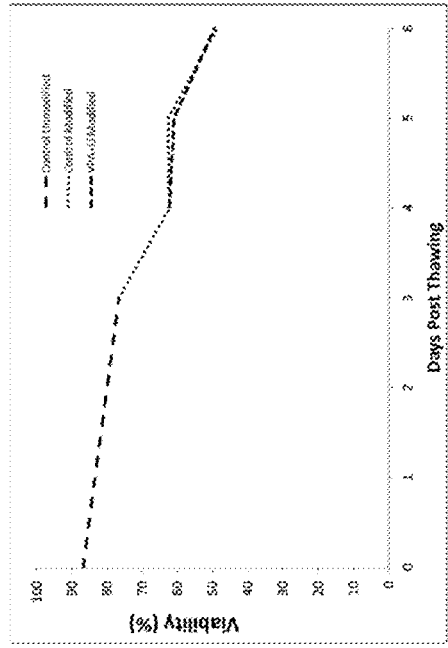
Figure 6D:
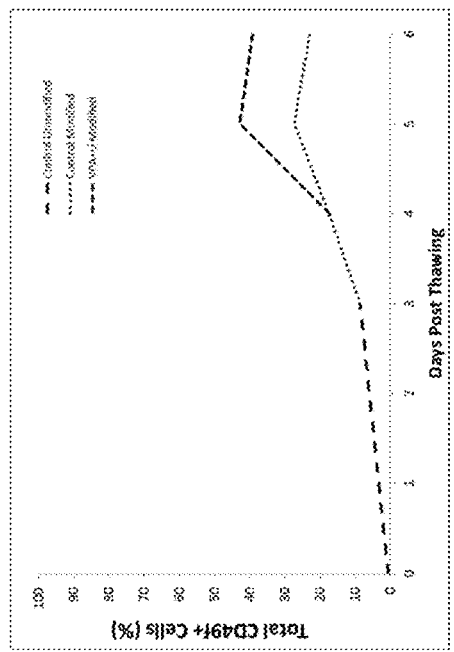
Figure 6F:
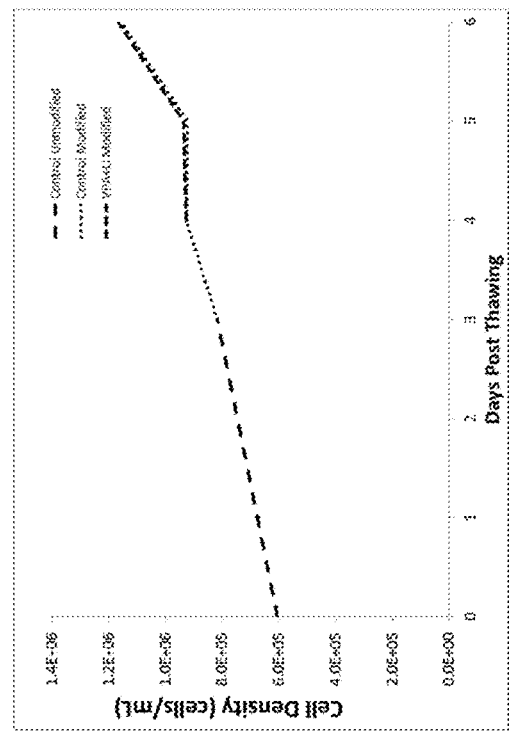

Furthermore, as shown in FIGS. 6A to 6D, VPA and Li addition after genomic modification increased CD90 expression (FIG. 6A), CD34 expression (FIG. 6B), CD133 expression (FIG. 6C) and CD49f expression (FIG. 6D) in both modified and unmodified cells. Cells retained high CD90, CD34, CD133 and CD49f expression after VPA washout and genome modification. In addition, as shown in FIG. 6E, no increased loss of cell viability was seen after VPA addition compared to controls until after genome modification, wherein a significant loss of viability was seen within 2 days in culture (as assayed by flow cytometry in the presence of propidium iodide). No change in culture cell density was seen after VPA addition compared to controls in genome modified mPB HSPCs (FIG. 6F).

Figure 6G:
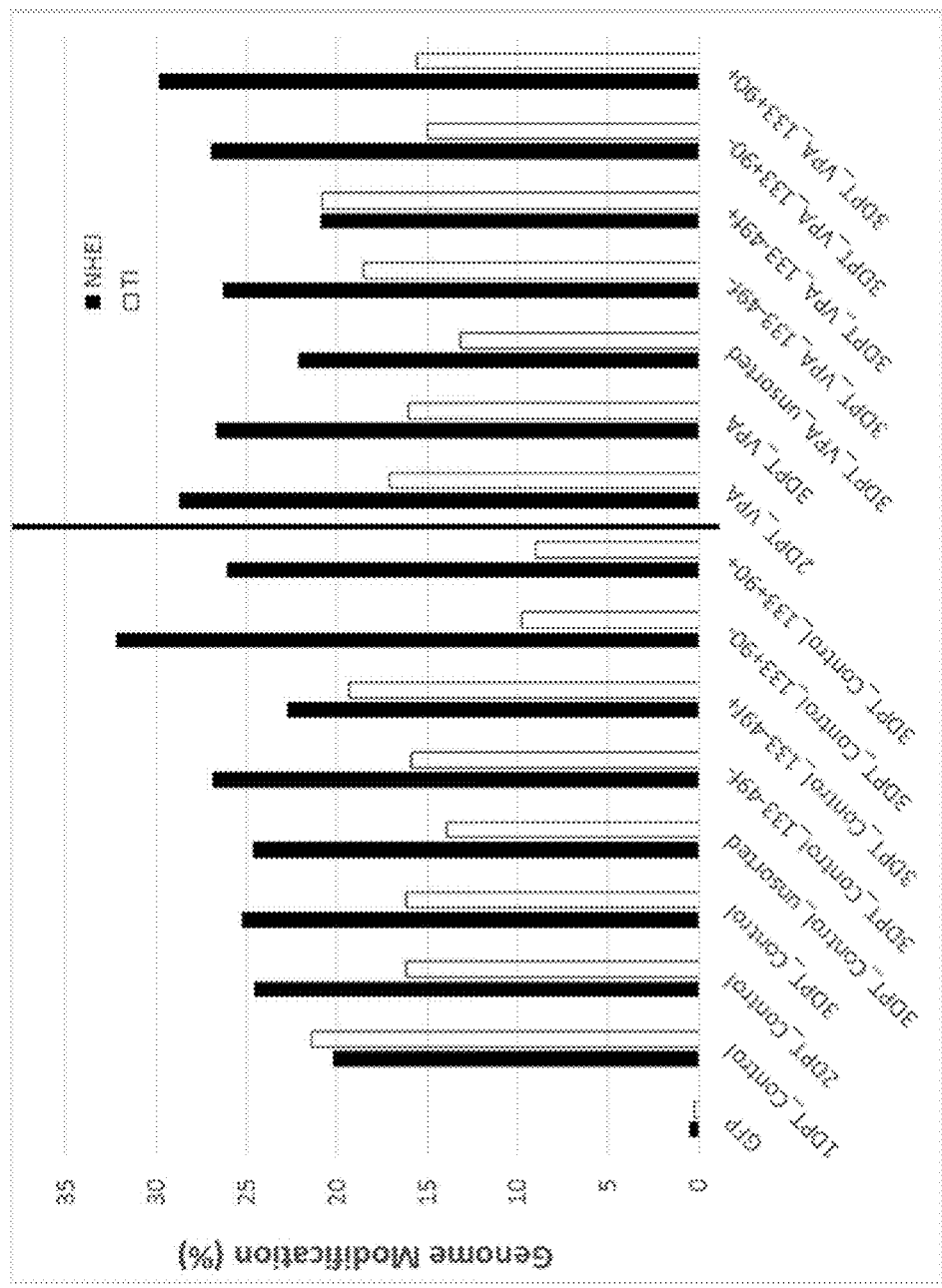
Figure 6H:
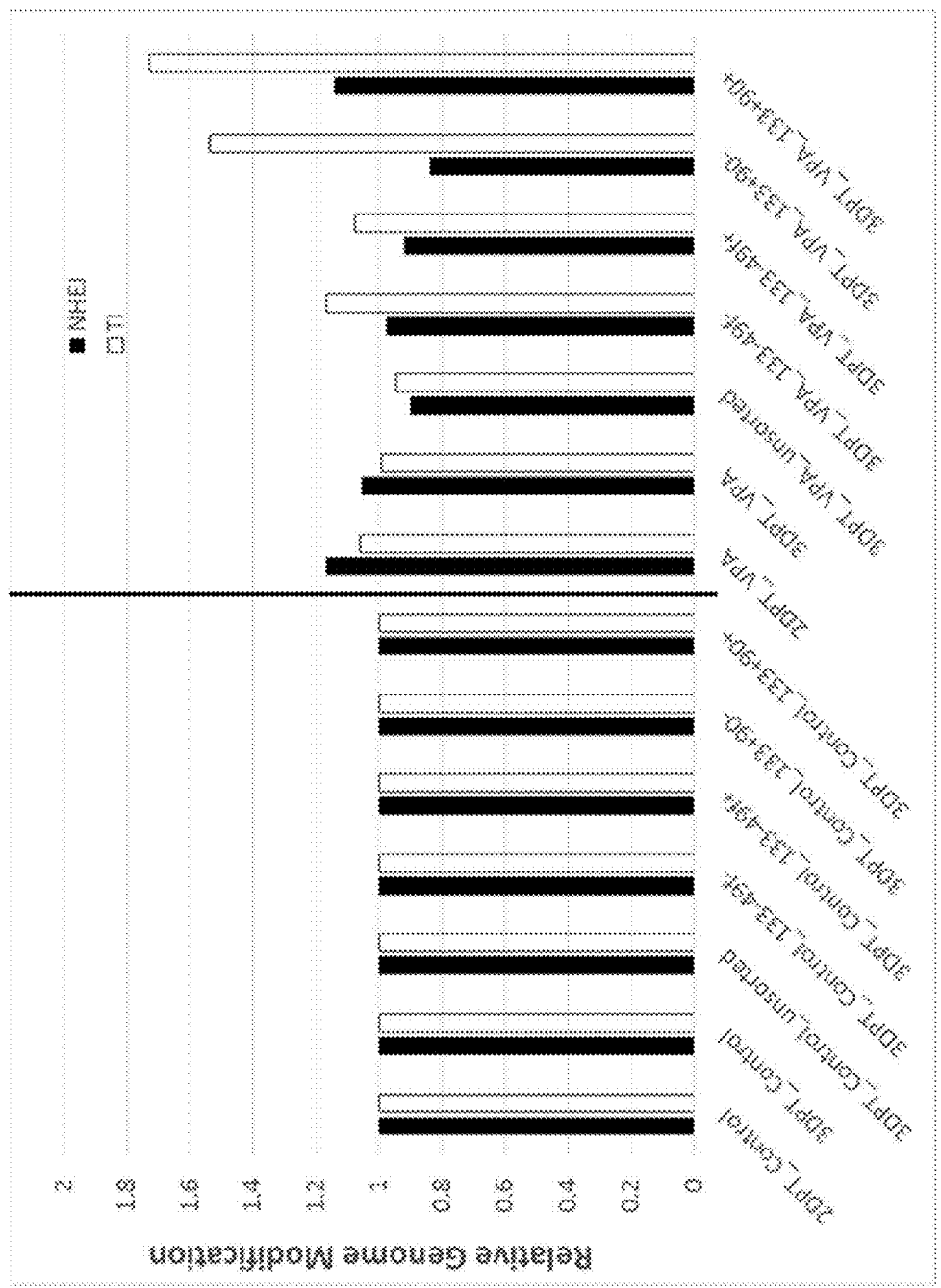

Miseq next-generation sequencing (NGS) of cell populations sorted by FACS showed no change in ZFN-mediated NHEJ in cells exposed to VPA+Li compared to controls (FIG. 6G). However, an increase in HDR-driven TI of the corrective cDNA transgene was seen, which was more pronounced in the more primitive cell populations. Cells transfected with CMV-GFP mRNA were used as a negative control. FIG. 6H shows relative genome modification of VPA-exposed cells to control cells.

These results demonstrated that VPA addition after genome modification in mPB-derived HSPCs enhanced multipotency and TI in more primitive cell populations and did not result in toxicity compared to controls.

Example 5

VPA Increases CRIPSR/Cas Nuclease Modification

Experiments are conducted as described in Example 3 using CRISPR/Cas nucleases in place of ZFNs (e.g., specific for any gene such as IL2, HPRT, etc.), with and without donors.

VPA or VPA/Li enhances CRISPR/Cas induced nuclease modification when introduced before, concurrently and/or after the CRISPR/Cas nuclease systems.

Example 6

Effects of IL-6, VPA Dosage and Time on HSPC Multipotency, Viability, and Proliferation Human mPB CD34+ cells were cultured ex vivo in CC110 media with or without 100 ng/mL IL-6 in the presence of VPA (1.25 mM or 2.5 mM) and 5 mM lithium chloride (Li) for 4 (blue lines—added at 4 days post thawing of the cells) or 7 days (red line—added at 1 day post thawing). At doses of 1.25 mM VPA, a loss of cell viability was seen only after VPA+Li addition, which was decreased substantially in the presence of IL-6. Cells treated with 2.5 mM VPA exhibited a substantial loss of cell viability with extended culture, which was minimized with decreasing doses of VPA. In addition, when VPA was added at day 1 post-thawing, VPA-treated cells showed increased CD34 expression as compared to cells where VPA was added at day 4 with extended culture. The results also showed a slight dose dependence on CD34 expression with increasing VPA doses. For CD133, CD90 and CD49f expression, cells in which VPA was added at day 1 reached and maintained a higher level of CD133, CD90 and CD49f expression as compared to cells with VPA added at day 4, indicating a fraction of cells (~15%) became unresponsive to VPA stimulation between days 1 and 4 post thawing.

The results also showed a dose dependence of CD90 and CD49f expression with increasing VPA. In particular, when VPA was added at day 1, cells reached and maintained a higher level of CD90 expression as compared to cells with VPA added at day 4, indicating a fraction of cells (~15% for CD133 and CD49f and ~20% for CD90) became unresponsive to VPA stimulation between days 1 and 4 post thawing. The presence of IL-6 was capable of enhancing the expression of CD49f with extended culture. No significant dose dependence on CD49f expression was seen with increasing VPA. In addition, a cell growth advantage was seen in cells exposed to VPA at day 4 compared to day 1 and a higher overall cell density in the absence of IL-6 was observed. Addition of 2.5 mM VPA resulted in a decreased cell growth potential, whereas lower doses did not affect cell growth as substantially. In a further experiment, human mPB CD34+ cells were cultured ex vivo in CC110 media in the presence of VPA (1.25 mM) plus LiCl (5 mM) with or without 100 ng/mL IL-6 for 7 days.

Figure 7:
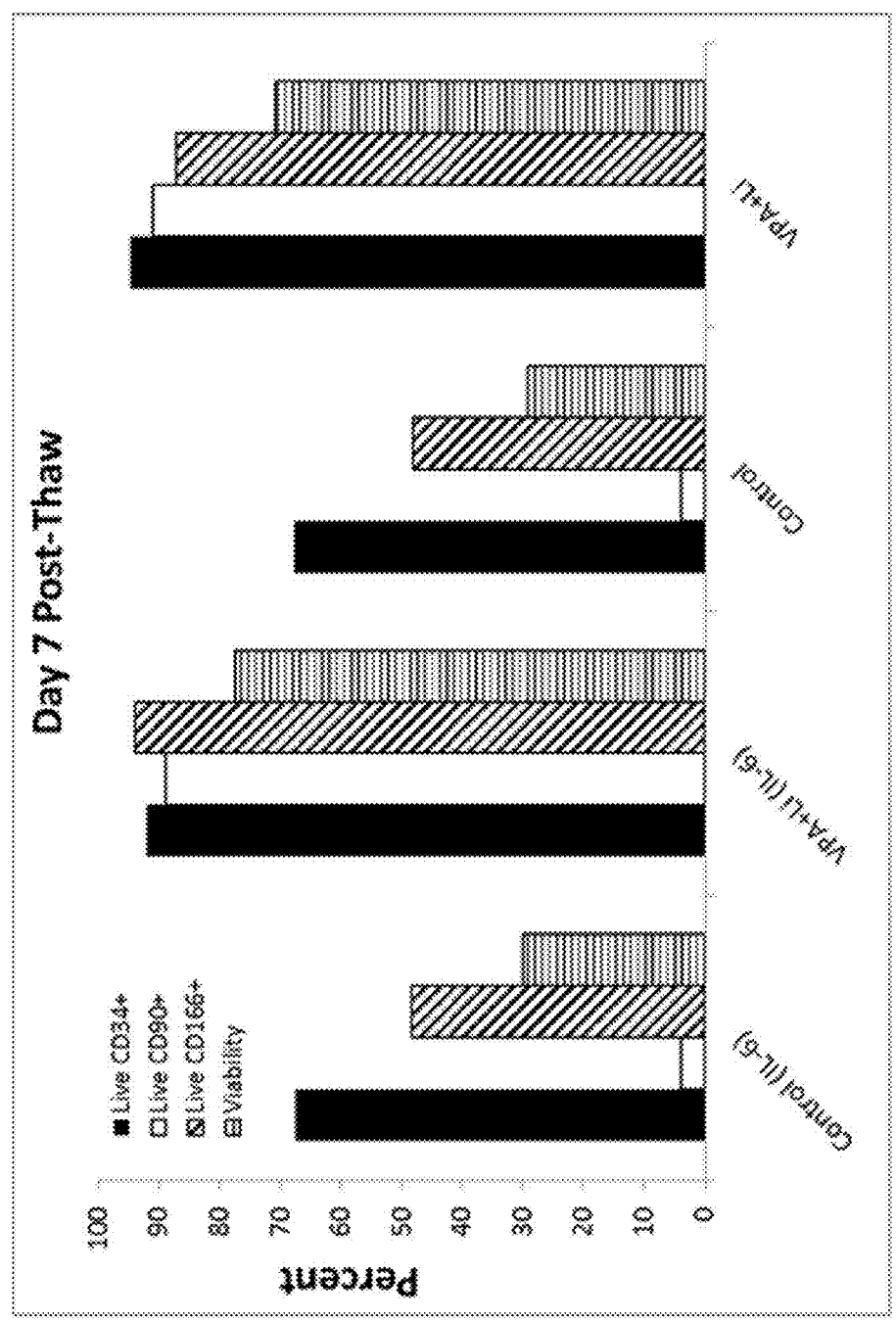
FIG. 7 is a graph showing the percent of live cells and cell viability under the indicated conditions. The left most bar of each group shows the percent of live CD34+ cells; the bar second from the left in each group shows the percent of live CD90+ cells; the bar second from the right in each group shows the percent of live CD166+ cells; and the right most bar of each group shows the cell viability.

VPA+Li dramatically increased CD90 expression after addition directly after thawing, reaching a peak within 2 days. In addition, VPA+Li retained elevated CD34 expression with extended culture compared to controls. VPA+Li also increased and maintained higher CD133 expression compared to controls. Furthermore, VPA also increased CD49f expression compared to controls. After 7 days in culture cells were stained using fluorescently-tagged antibodies against the HSPC multipotency marker CD166 (PE) and analyzed by flow cytometry. VPA+Li increased the overall fraction of CD166+ cells. FIG. 7 shows that VPA+Li increases the overall fraction of CD166+, CD90+, and CD34+ cells compared to controls after 7 days in culture.

Human mPB CD34+ cells were cultured ex vivo in CC110 media with 100 ng/mL IL-6 in the presence or absence of VPA (1.25 mM) plus LiCl (5 mM) for 6 days. Cells were then stained with 5 different antibodies (CD34, CD38, CD45RA, CD90, and CD49f) and gated on the CD34+CD38−CD45RA−CD90+CD49f+ population, which has been shown to have a high level of long-term repopulating HSCs. This fraction was dramatically increased in the presence of VPA plus LiCl.

Figure 8:
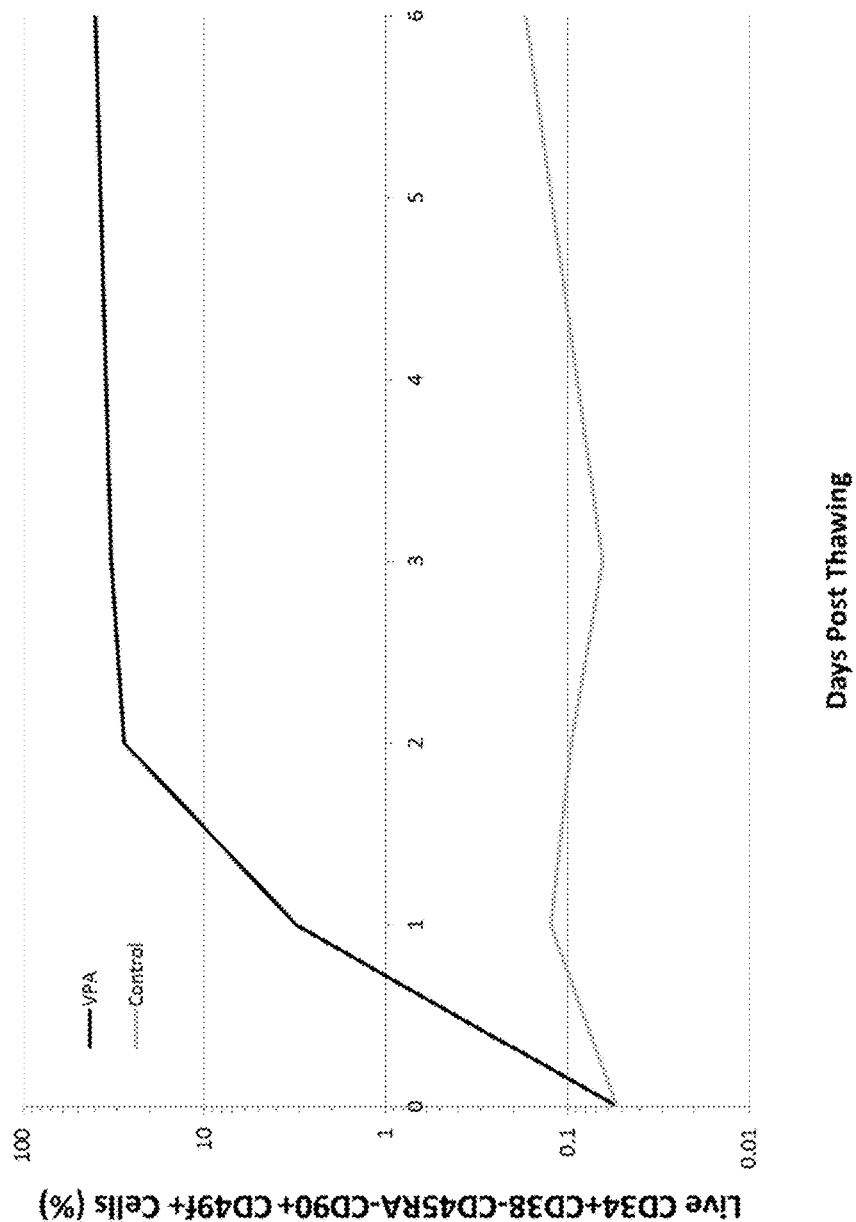
FIG. 8 is a graph showing the percent of live cells which are CD34+, CD38−, CD45RA−, CD90+, and CD49f+ in control or VPA+LiCl treated cultures over the course of 6 days. This quintuple set of markers is characteristic of long-term repopulating HSCs (LT-HSC).

FIG. 8 shows the percent of live cells which are CD34+, CD38−, CD45RA−, CD90+, and CD49f+ in control or VPA+LiCl after 6 days of culture.

Analysis of cell viability (assayed by flow cytometry in the presence of propidium iodide) showed an initial delay in recovery following VPA administration and overall slightly lower viability with VPA. Similarly, VPA administration resulted in an initial slightly decreased proliferative capacity, but recovered after 7 days in culture.

Thus, VPA increased HSC multipotency marker expression, which was enhanced in the presence of IL-6.

Example 7

Identification of the Nature of the Inhibition of Homology-Directed Repair (HDR) in LT-HSC To determine the underlying cause in poor target integration and gene correction in LT-HSC, several approaches are taken. The different sub-pools within the CD34+ population are sorted following editing according to the conditions described below into three sub-pools: CD34+, CD133−, CD90-low; CD34+, CD133+, CD90-low; and Cd34+, CD133+, CD90-high. Other cell-surface marker expression patterns known in the art to correlate with the LT-HSC phenotype are also used, including, by way of non-limiting example, CD38− and CD49f-low. The conditions used are:
1. Investigation of Poor Transfectability.

CD34+ cells are transfected with mRNA encoding GFP and the percent of GFP expression in each CD34+ sub-pool measured. In addition, the cells are transfected with mRNA encoding ZFNs and the stability of the expressed ZFN proteins is measured over time using anti-Fok1 antibodies. To collaborate and extend these measurements, the level of mRNA in the transfected is analyzed using qRT-PCR using methods known in the art. These data determine the relative stability of mRNA and expressed protein in the CD34+ pools as well as the amount of transfection observed for each cell type. Based on these results, optimal transfection conditions are selected.
2. Poor Expression or Stability of the ZFNs.

It has been suggested that protein synthesis in HSC is lower than in other hematopoietic cell types (see Signer et at (2013) Nature 509(7498): 49-54). Thus, the mean fluorescence intensity of the GFP and ZFN transfected cells is analyzed in the three subpools. Additionally, stability of the ZFN proteins is analyzed over time using anti-Fok 1 or anti-FLAG antibodies by Western blot using methods know in the art to insure that any observed fluorescent signal is derived from intact ZFNs. Based on these results, optimal time conditions are selected. If mRNA stability and/or expression are determined to be a cause of poor expression, cis-active sequences are added to the ZFN mRNA to improve stability and/or translation. Non-limiting examples of such cis-active sequences used are disclosed in the art, e.g. Knapinska et at (2005) Curr Genom 6(6): 1.
3. Delivery of Donor DNA.

In the case where donor DNA is provided by transfection, to test the theory that LT-HSC modification is correlated with delivery of donor DNA, the amount of donor DNA actually delivered is measured in the different pools using qPCR by methods known in the art. Further, transfection parameters such as voltage, pulse length, and pulse shape are optimized. These tests will determine the transfectability of large donors used for targeted integration. Small oligonucleotides are the least likely to be affected by delivery parameters however. Using the results, optimal concentrations of donor are selected for delivery.

In the case where donor DNA is provided by infection of CD34+HSPCs by a virus, to test the theory that poor LT-HSC modification is due to poor delivery of donor DNA, the type of virus (AAV, lentivirus, adenovirus, e.g.), the serotype or pseudotype of virus, and the dose (MOI) of virus is optimized. Using these results, optimal viral types and doses are selected for LT-HSC transduction with donor DNA.
4. Induction of the DNA Damage Response.

In order for targeted integration and gene correction to occur in the stem cells, the DNA damage response must be initiated following nuclease cleavage. The DNA damage response is a pre-requisite for the chromatin remodeling that is needed for efficient homology dependent repair (HDR). To characterize the amount and time scale of the DNA damage response, CD34+ cells are transfected with ZFN encoding mRNA and then the formation of 53BP and H2AX (indicative of residual DSB) foci are measured in the three cell pools by standard methods known in the art. Using the results obtained, optimal timing and concentrations of mRNAs are selected.
5. Repair Pathway of Choice by the Cells (NHEJ Vs. HDR).

To increase the frequency of knock-out, it is important to increase the likelihood of the cell using the error-prone NHEJ process following nuclease cleavage. However, to increase the frequency of both gene correction (alteration) and/or targeted insertion, it is important to increase the likelihood of HDR. Thus, the choice of repair pathway following DNA cleavage in the three cell pools is monitored using the "traffic light" reporter system (see Certo et at (2012) *Nat Meth* 9(10):973-975). Briefly, a 'traffic light reporter' is devised comprising a nuclease target site within a fluorescent T2A.mCherry gene in the +3 ORF and a GFP reporter gene in the +1 reading frame such that repair completed by HDR will result in a GFP positive cell while repair completed by NHEJ will result in a mCherry positive cell. Cells are assayed by flow cytometry or any other method known in the art to quantitate fluorescent signal. Thus, the results of the experiments are used to select conditions corresponding to the desired repair outcome.

6. Analysis of Cell Cycle State.

Cell cycle status is also known to influence the repair pathway utilized by the cell (NHEJ versus HDR as discussed above). Thus, cell cycle state will be analyzed in the three cell pools using various methods known in the art. This analysis will evaluate the effectiveness of treatments thought to assist in stem cell expansion such as SR-1, dmPGE2, rapamycin, UM171, UM759, Notch/delta/ANGPTL5, Tat-myc and tat-Bcl2 fusion proteins, and MAPL14/p38a Ly2228820 by way of non-limiting example.

Concentrations and combinations of these factors, in addition to varying exposure lengths (e.g. exposure from 24 up to 48 and up to 72 hours and any value therebetween) will be analyzed with respect to cell cycle and effect on HDR frequency by methods known in the art (for example, insertion of a reporter transgene comprising homology arms or insertion of an oligonucleotide comprising an RFLP for integration via HDR). The factors are evaluated with regard to the desired maintenance of stemness in the CD34+ sub pools. The results of these experiments are used to select conditions corresponding to the desired outcome.

7. Performance of RNAseq on the Three Gene Pools Following the Varying Treatments to Analyze Gene Expression Signatures Associated with HSC Sub-populations Proficient in the Desired Genome Editing Pathways.

Using methods known in the art (see for example Wang et at (2009) *Nat Rev Genet* 10(1): 57-63), the HSC subpopulations are treated with the factors described above regarding the cell cycle state at varying concentrations, combinations and exposure times and analyzed for expression profiles. The results are used to select the optimum conditions relating to the desired outcome.

The results of all these studies are considered and a protocol optimizing the desired outcome in LT-HSC is identified.

In addition, the cells are studied for use in large scale production of edited LT-HSC. Bulk CD34+ cells are pre-stimulated with cytokines comprising Stemspan™ CC110, Flt-3 ligand, SCF, and TPO and all combinations thereof in concentrations from 10 ng/mL to 1000 ng/mL. Prestimulation may require exposure times of 24, up to 48 and up to 72 hours. For clinical-scale HSPC transfection, any high capacity system may be used (e.g. Maxcyte GT Flow Transfection System).

Example 8

Engraftment

The edited LT-HSC are subjected to colony forming assays in methylcellulose medium to confirm the frequency of pluripotent cells and to verify that the colonies possess the desired genetic editing at the expected frequencies. The methylcellulose studies are carried out using methods known in the art (see for example Keller et al (1993) *Mol Cell Bio* 13(1):473).

Further, the modified LT-HS cells are engrafted into a relevant mouse model and/or a non-human primate model (e.g., the NOD/SCID/IL2r$\gamma^{null}$ (NSG) mouse). Engraftment in these animals is done according to methods known in the art. See, for example Holt et al (2010) *Nat Biotech* 28, 839-847, Ho et al (2009) *Retrovirology* 6:65 and Peterson et al (2014) *J. Med Primatol* 42: 237.

The methods identified in these studies are used to insert a transgene of interest into a non-human primate (see above) to evaluate the engraftment potential of gene modified CD34+LT-HSC in an autologous transplant model. Engraftment with (1020 cGy irradiation) or without (200 cGy irradiation) myeloablative preconditioning is used to investigate optimum engraftment and expansion conditions for stem cell transplantation. Results from the experiments are used to determine optimum conditioning.

Example 9

Ex Vivo Administration of Genetically Modified Cells

The genetically modified cells (e.g., stem cells) as described herein are given in a bone marrow transplant to a subject such that the cells differentiate and mature in vivo. The HSC/PCs that are genetically modified as described herein may be isolated following G-CSF or plerixafor-induced mobilization and/or the cells may be isolated from human bone marrow or umbilical cords. The genetic modification may be inactivation or one or more genes, integration of one or more donors and/or replacement of one or more gene sequences (e.g., aberrantly-expressed or other mutant sequences). The patient may be subject to mild or full myeloablative pre-conditioning prior to administration of the genetically modified cells.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A cell culture comprising:
   a stem cell comprising an exogenous nuclease that cleaves the genome of the stem cell;
   interleukin 6 (IL-6);
   lithium chlorine (LiCl); and
   a histone deactylase inhibitor (HDACI), wherein the HDACI is valproic acid (VPA) at a concentration of between 1.25 and 5 mM.

2. The cell culture of claim 1, wherein the stem cell further comprises a donor sequence.

3. A method for preparing a cell culture according to claim 1, wherein the stem cells comprise exogenous nucleases that cleave the genomes of the stem cells, the method comprising
   culturing the stem cells in the presence of the histone deactylase inhibitor (HDACI) wherein the HDACI is valproic acid (VPA) at a concentration of between 1.25 and 5 mM; interleukin 6 (IL-6); and lithium chlorine (LiCl).

4. The method of claim 3, further comprising introducing one or more exogenous donor sequences into the stem cells such that the donor molecule is introduced into the genomes of the cells following cleavage by the nuclease.

5. The method of claim 3, wherein the exogenous nucleases are delivered to the stem cells as a nucleic acid encoding the nuclease.

6. The method of claim 5, wherein the nucleic acid is mRNA.

7. The method of claim 3, wherein the exogenous nuclease is selected from the group consisting of a zinc finger nuclease (ZFN), a TALE-nuclease (TALEN), a CRISPR/Cas nuclease system or combinations thereof.

8. The method of claim 4, wherein the donor sequences comprise a sequence selected from the group consisting of sequences encoding a protein, regulatory sequences, sequence that encode a structural nucleic acid such as a microRNA or siRNA.

9. The method of claim 8, wherein the protein is selected from the group consisting of a regulatory protein that modulates expression of a gene; an antibody, an antigen, an enzyme, a growth factor, a receptor, a hormone, a lymphokine, a cytokine, a reporter and combinations thereof.

* * * * *